US012802811B2

(12) United States Patent
Simmons et al.

(10) Patent No.: US 12,802,811 B2
(45) Date of Patent: Nov. 17, 2026

(54) CARE VILLAGE DIGITAL TWIN SYSTEM AND METHOD

(71) Applicant: LogicMark, Inc., Louisville, KY (US)

(72) Inventors: Chia-Lin Simmons, Louisville, KY (US); Rafael Saavedra, Louisville, KY (US); Peter Williams, Louisville, KY (US)

(73) Assignee: LogicMark, Inc., Louisville, KY (US)

( * ) Notice: Subject to any disclaimer, the term of this patent is extended or adjusted under 35 U.S.C. 154(b) by 0 days.

(21) Appl. No.: 18/511,726

(22) Filed: Nov. 16, 2023

(65) Prior Publication Data

US 2024/0177853 A1 May 30, 2024

Related U.S. Application Data

(60) Provisional application No. 63/385,592, filed on Nov. 30, 2022.

(51) Int. Cl.
*G16H 40/67* (2018.01)
*G06F 21/62* (2013.01)
*G16H 50/20* (2018.01)

(52) U.S. Cl.
CPC ......... *G16H 40/67* (2018.01); *G06F 21/6245* (2013.01); *G16H 50/20* (2018.01)

(58) Field of Classification Search
None
See application file for complete search history.

(56) References Cited

U.S. PATENT DOCUMENTS

2015/0169314 A1* 6/2015 Dicks .................... G06F 8/61 713/2
2019/0166101 A1* 5/2019 Ramos .................. H04L 9/3239
2020/0170711 A1* 6/2020 Hendriks ........... A61B 5/14503
2021/0045682 A1* 2/2021 Poon ...................... G16H 50/20

OTHER PUBLICATIONS

Ramasamy LK, et al. Secure Smart Wearable Computing through Artificial Intelligence-Enabled Internet of Things and Cyber-Physical Systems for Health Monitoring. Sensors (Basel). Jan. 29, 2022;22(3):1076. doi: 10.3390/s22031076. PMID: 35161820; PMCID: PMC8840137. (Year: 2022).*

PCT/US2023/080123, "International Search Report and the Written Opinion", Mar. 28, 2024, 11 pages.

Ramasamy et al., "Secure Smart Wearable Computing through Artificial Intelligence-Enabled Internet of Things and Cyber-Physical Systems for Health Monitoring", Sensors, Available Online at: https://www.mdpi.com/1424-8220/22/3/1076, Jan. 29, 2022, 16 pages.

* cited by examiner

*Primary Examiner* — Katherine Kolosowski-Gager
(74) *Attorney, Agent, or Firm* — K&L Gates LLP

(57) ABSTRACT

A system of entities is represented by digital twins. Each digital twin incorporates specifications of the capabilities of the entity. Each digital twin incorporates the physical characteristics of the entity. Each digital twin represents the state of the entity. The interactions between digital twins provide an accurate and timely representation of the interactions between the entities.

19 Claims, 18 Drawing Sheets

Example of CVDT for Device(s)

FIG. 1 CVDT Execution environment
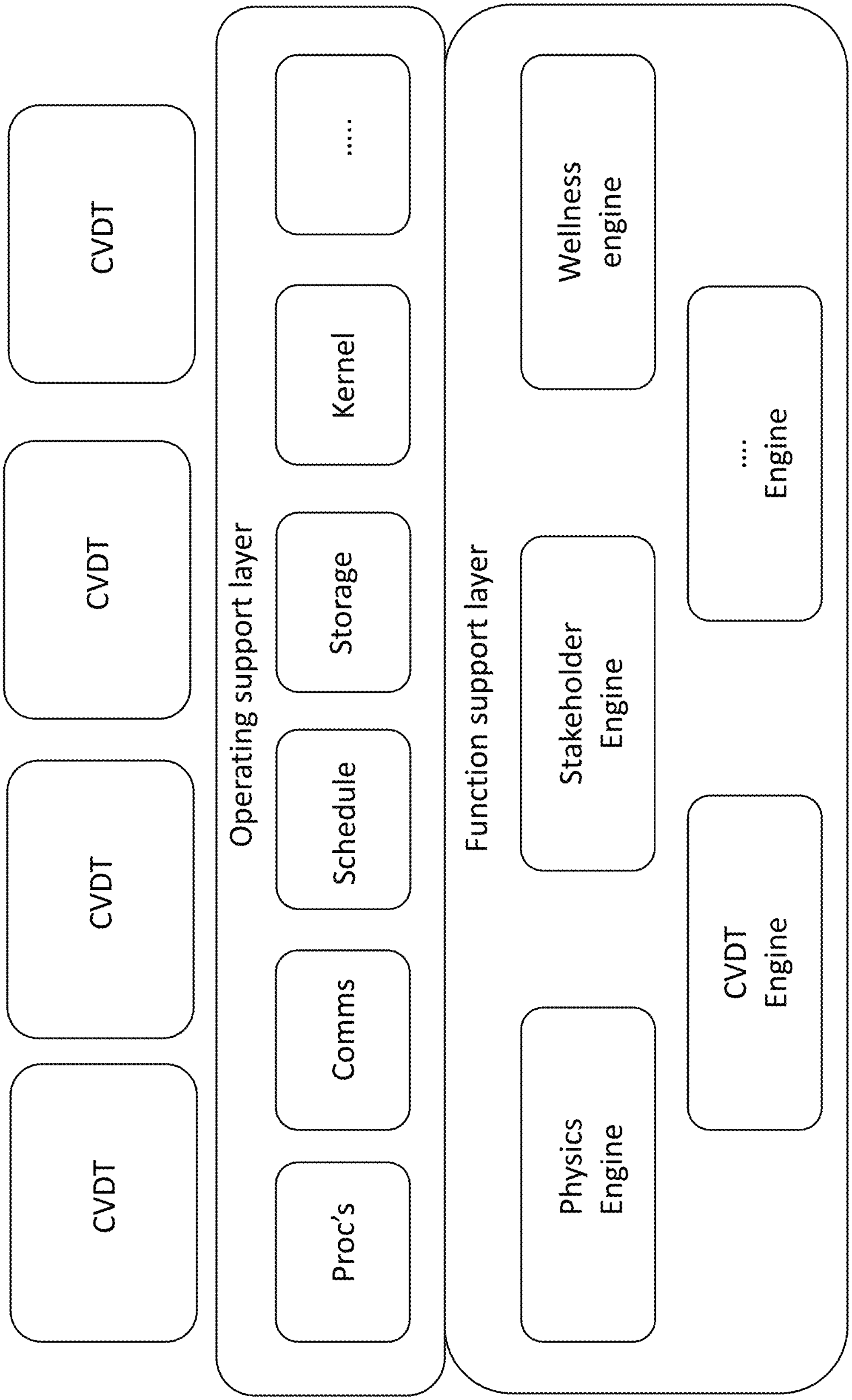

FIG. 2 Example of CVDT for Stakeholder
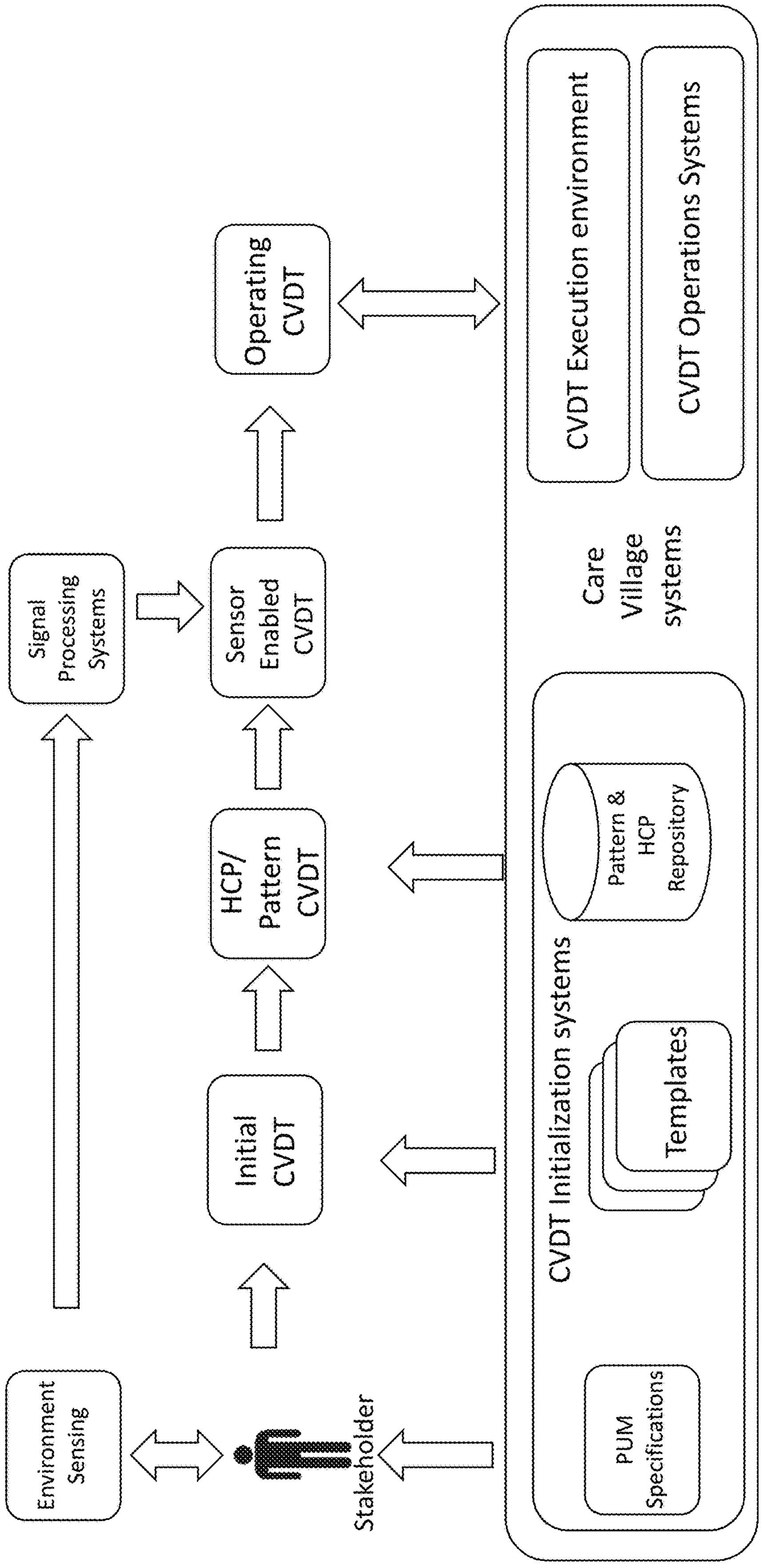

FIG. 3 Example of CVDT for Device(s)
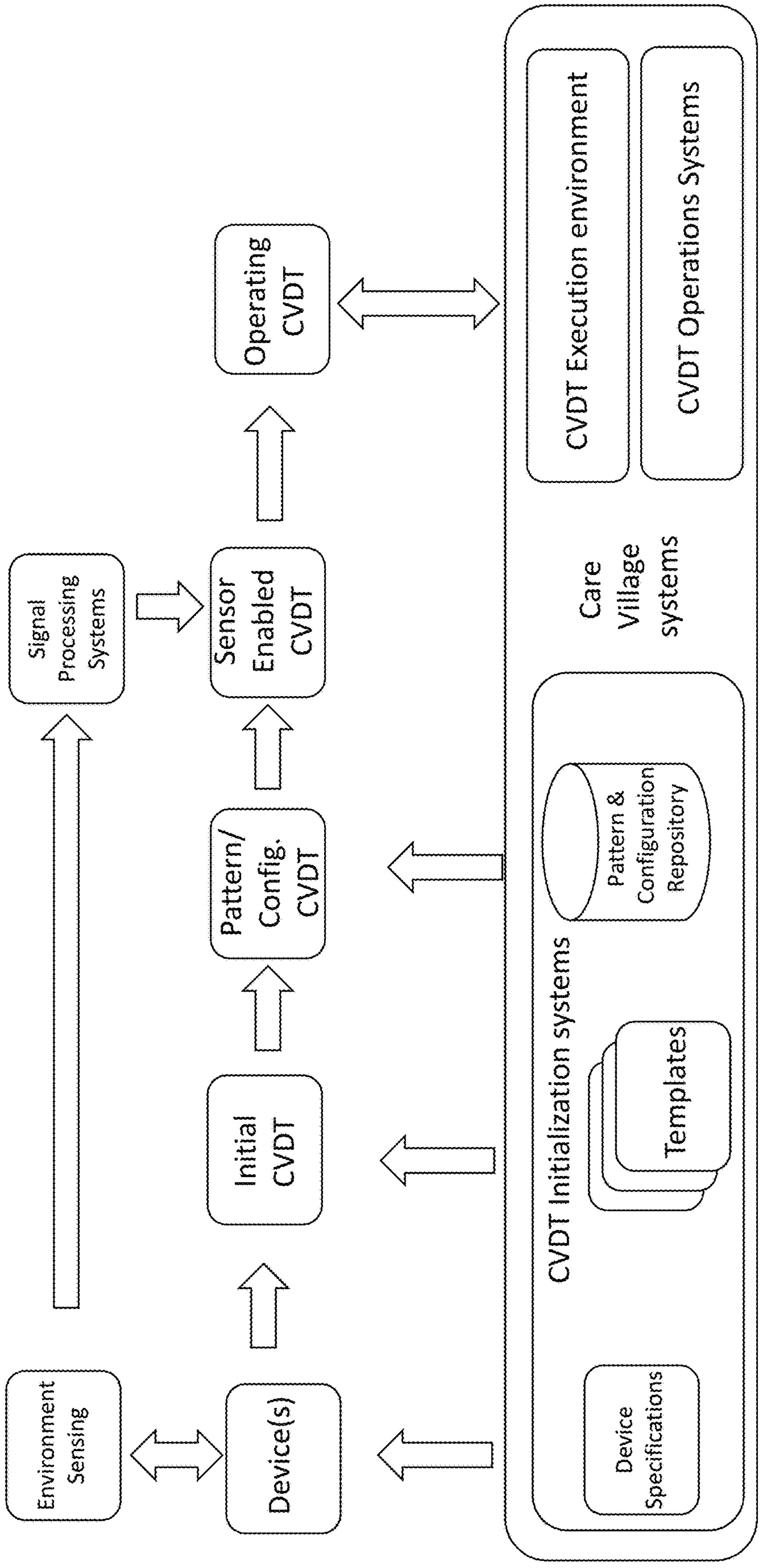

FIG. 4 Example of CVDT for Environment
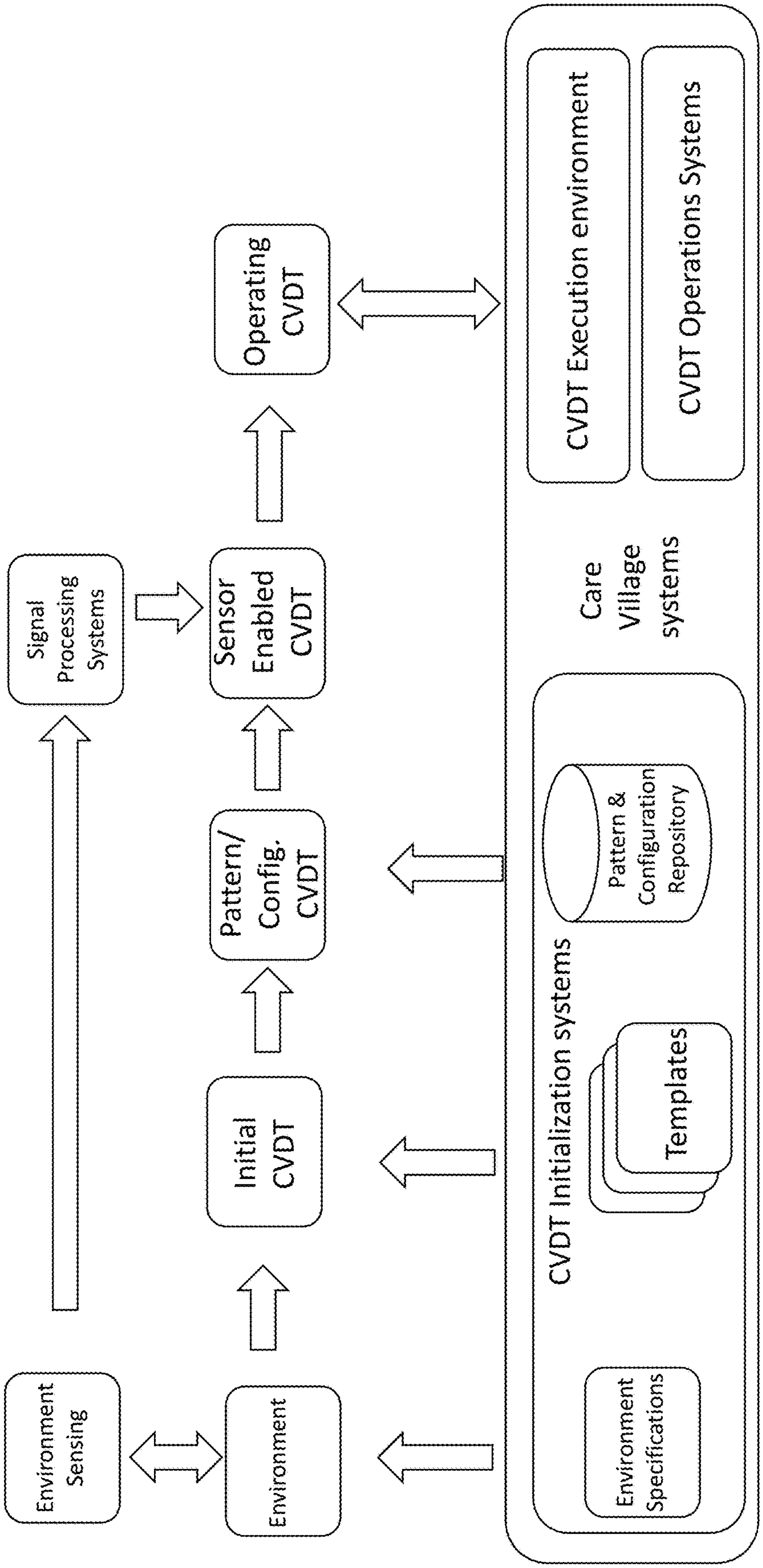

FIG. 5 CVDT at differing times
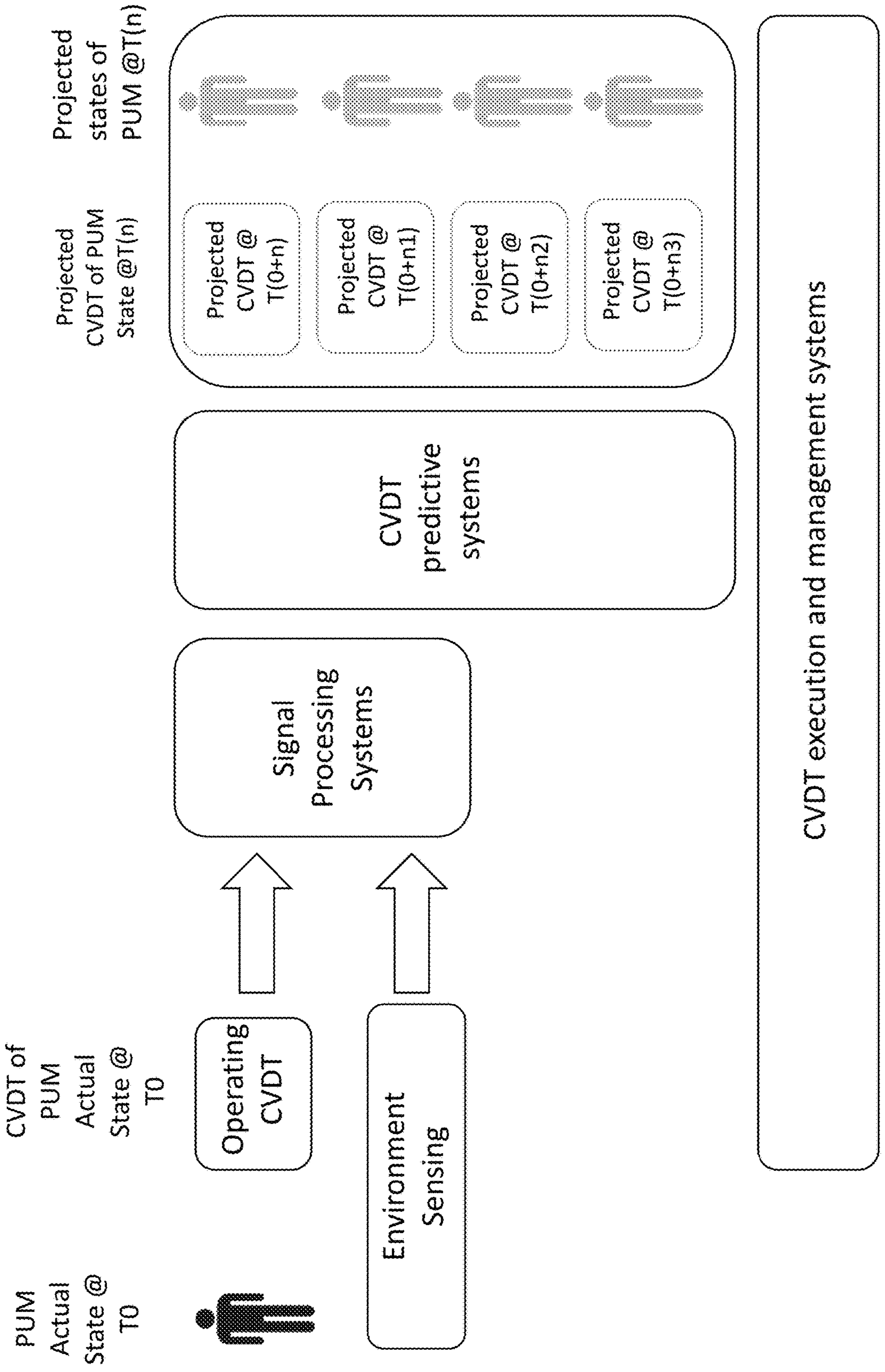

FIG. 6 alternative predicted CVDT
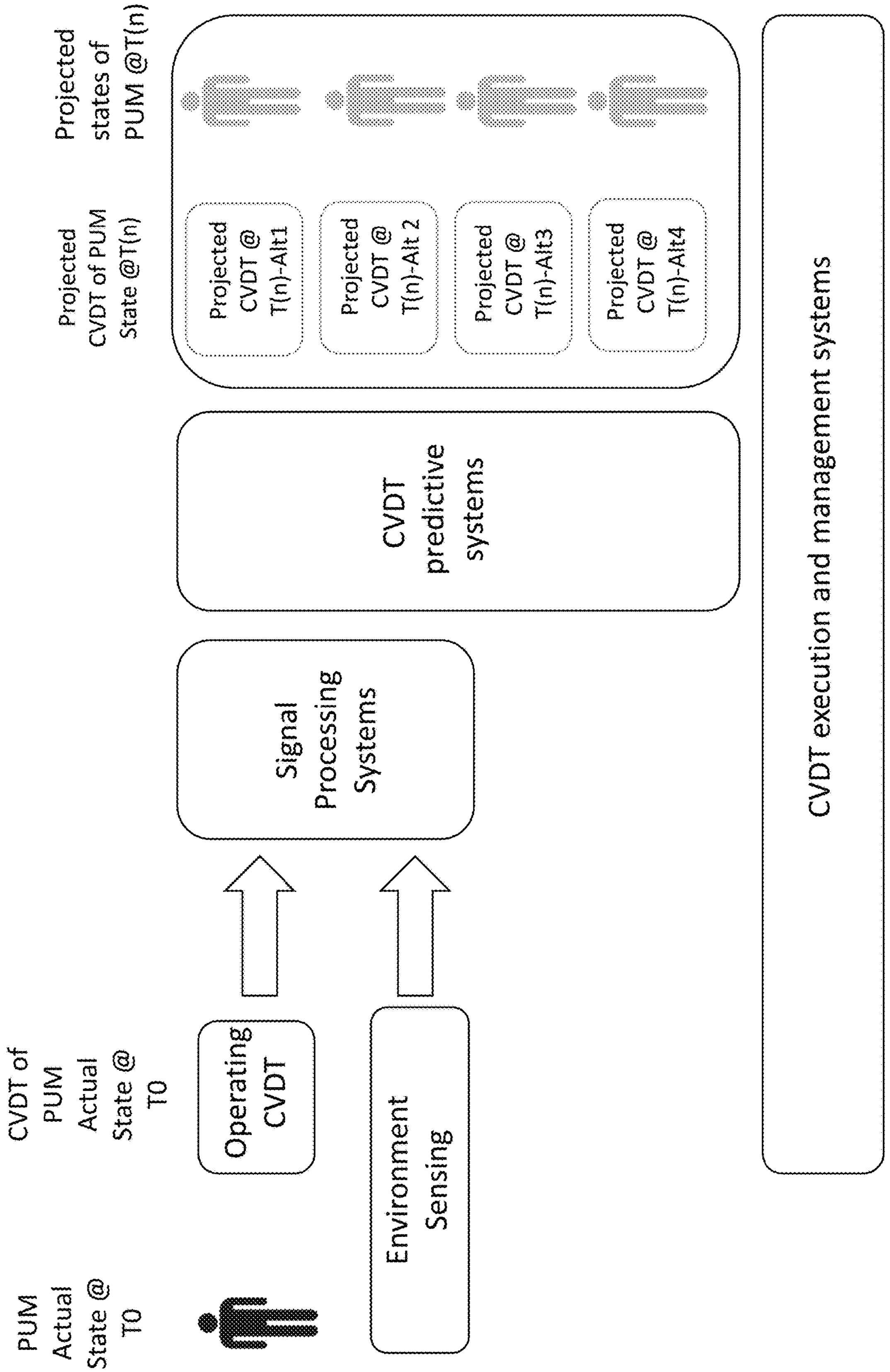

FIG. 7 alternate and linear predicted CVDT
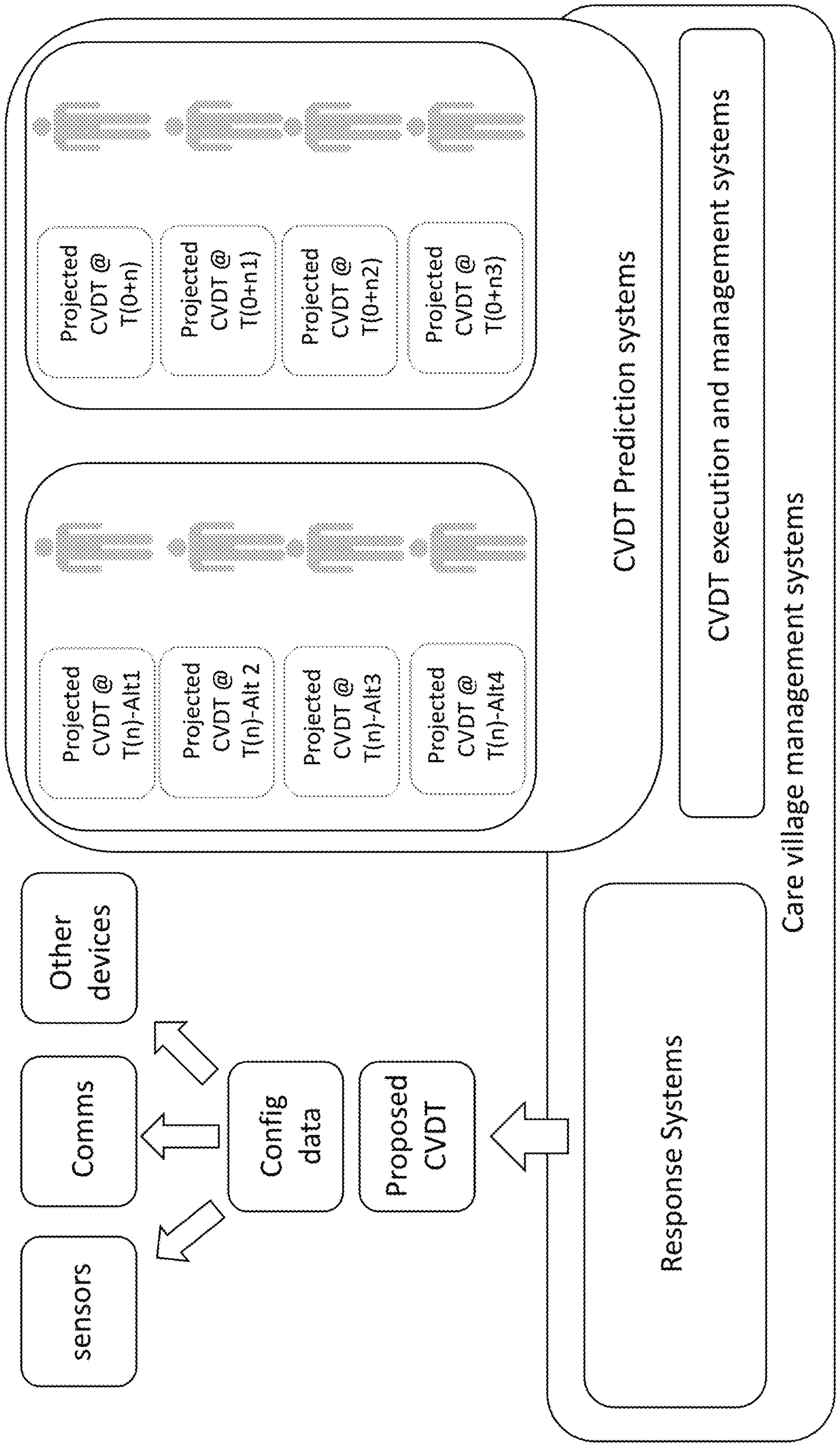

FIG. 8 predicted states of PUM
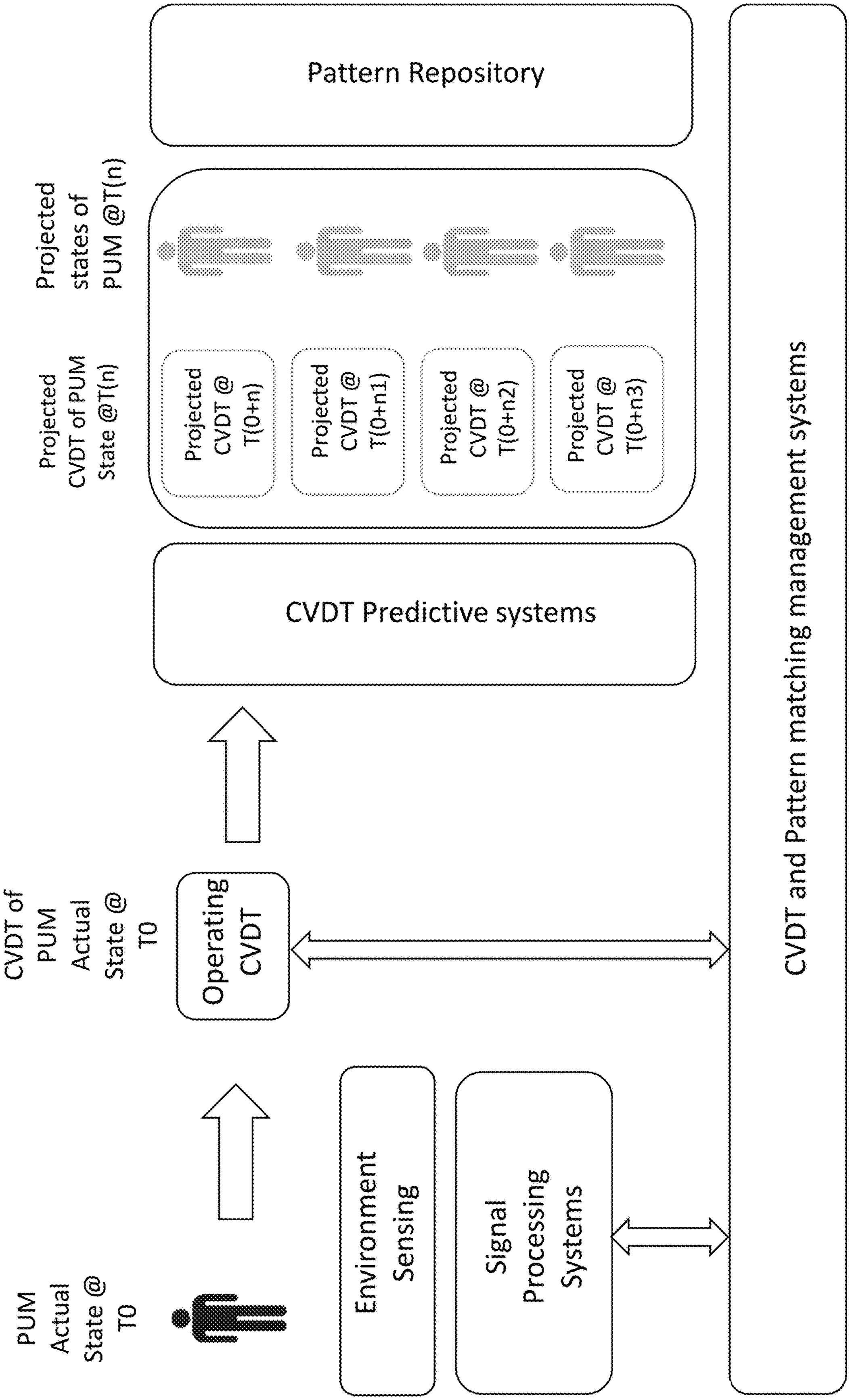

FIG. 9 predicted CVDT with configurations
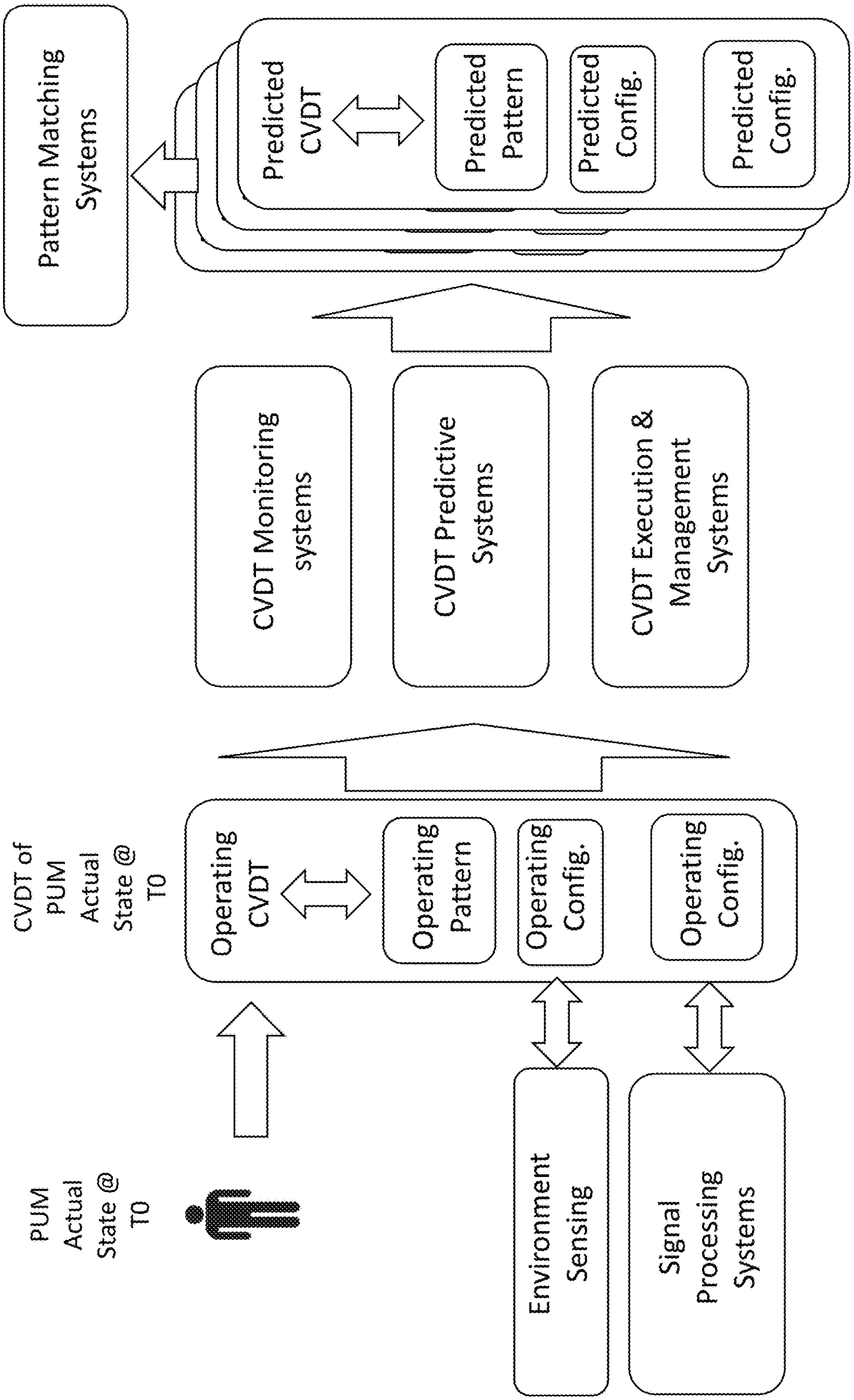

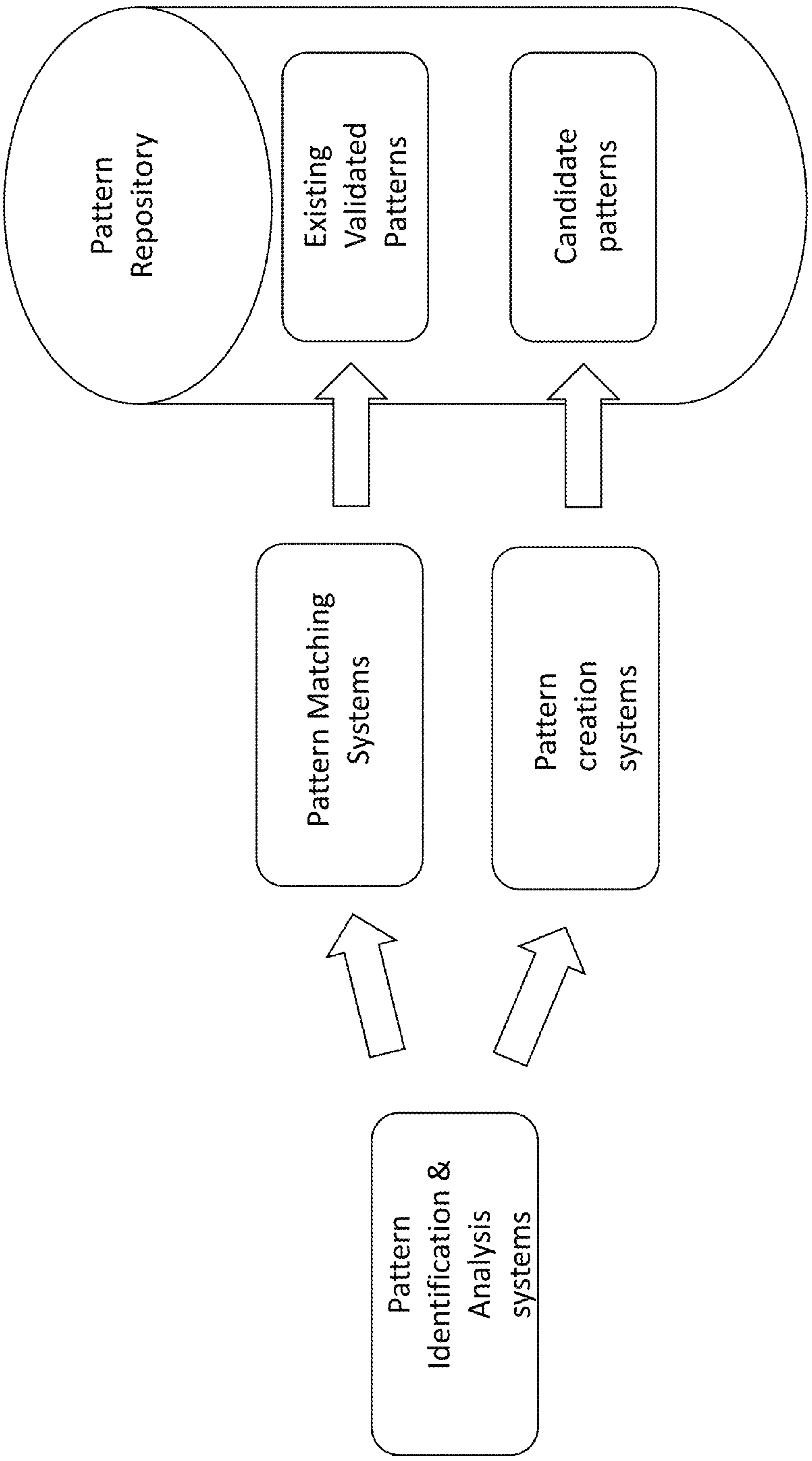
FIG. 10 pattern identification, matching and creation systems

FIG. 11 CVDT system
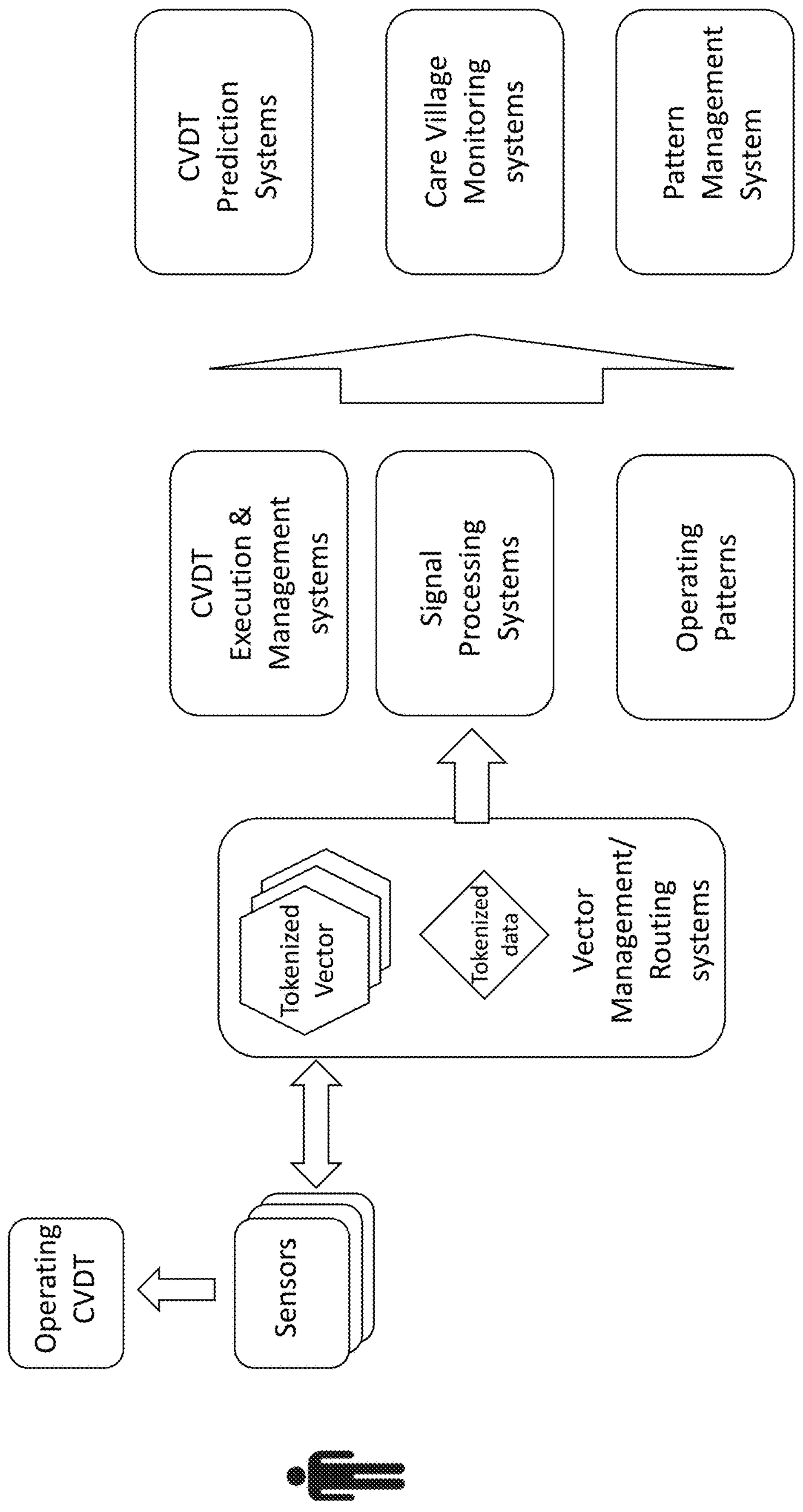

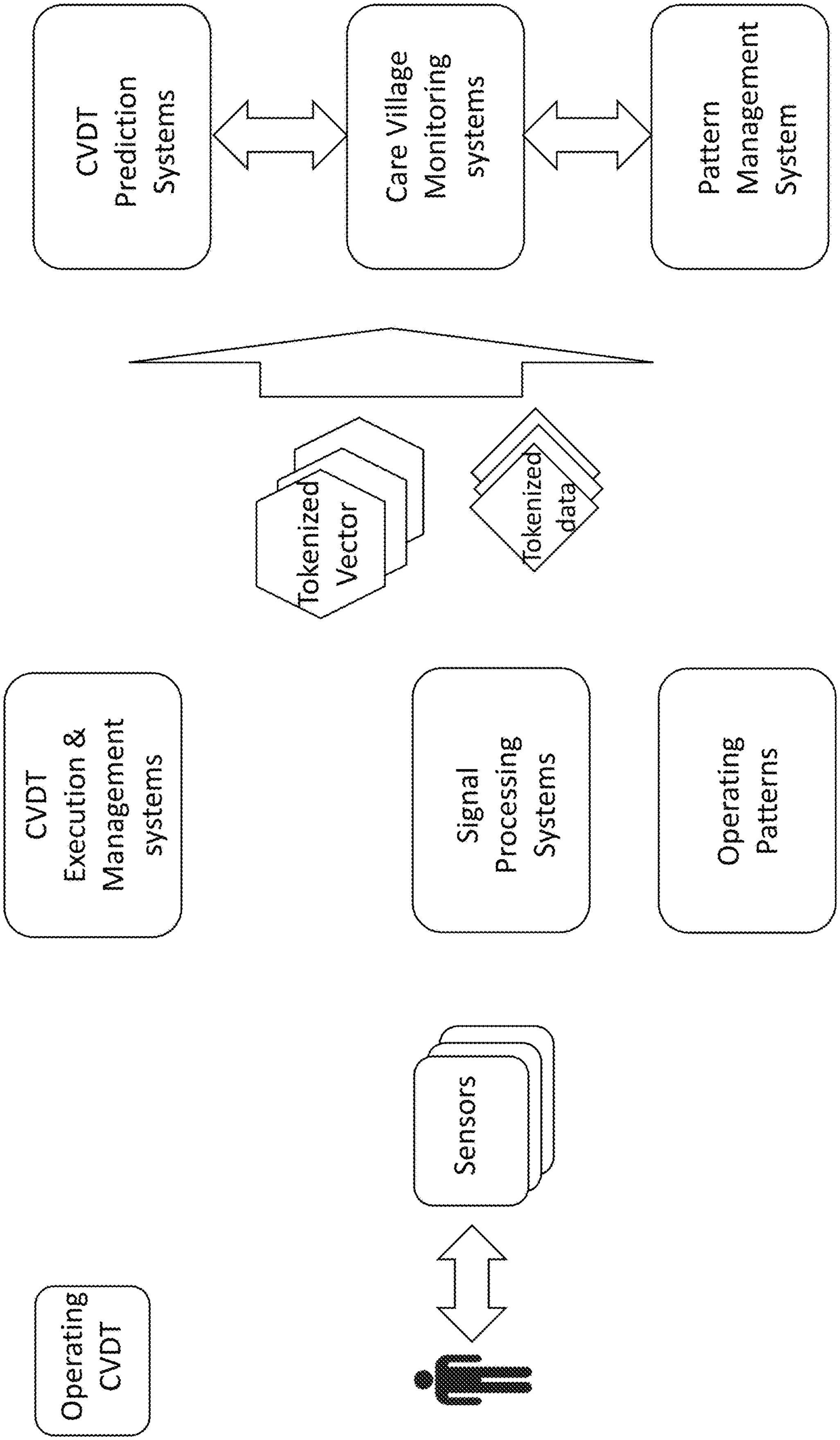
FIG. 12 CVDT system

FIG. 13 CVDT predictions
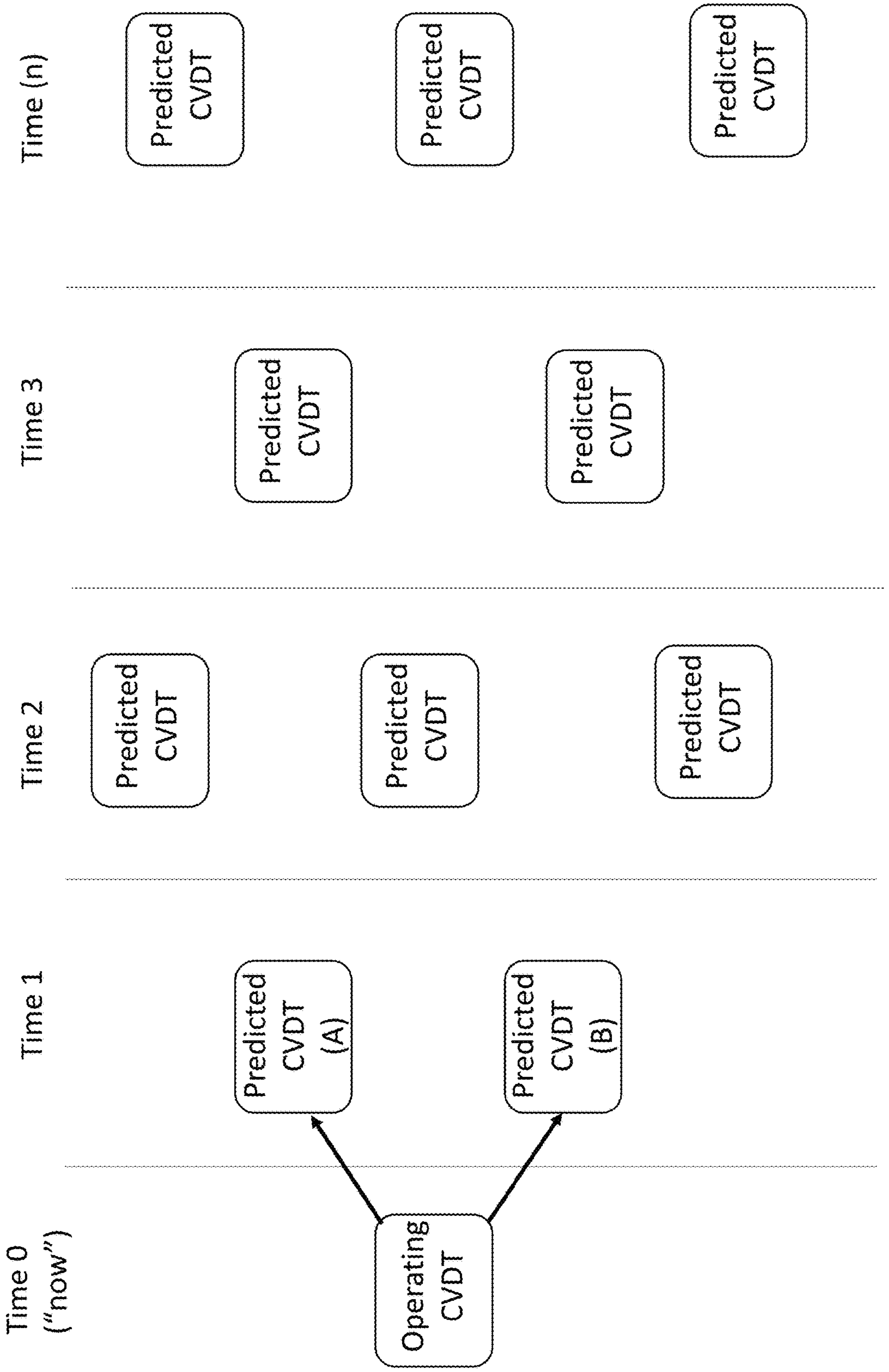

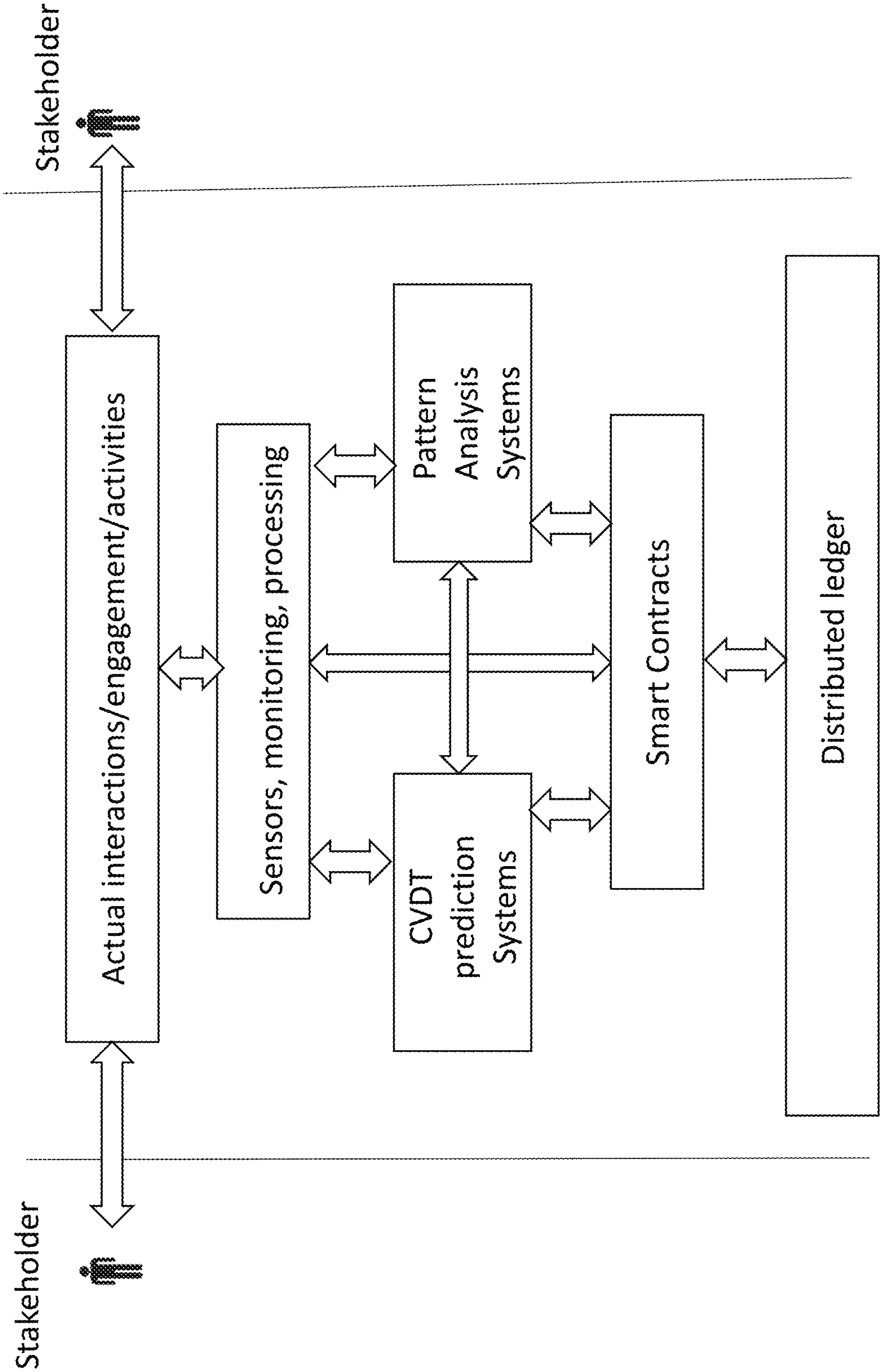
FIG. 14 Pattern Analytics

FIG. 15 CVDT simulations
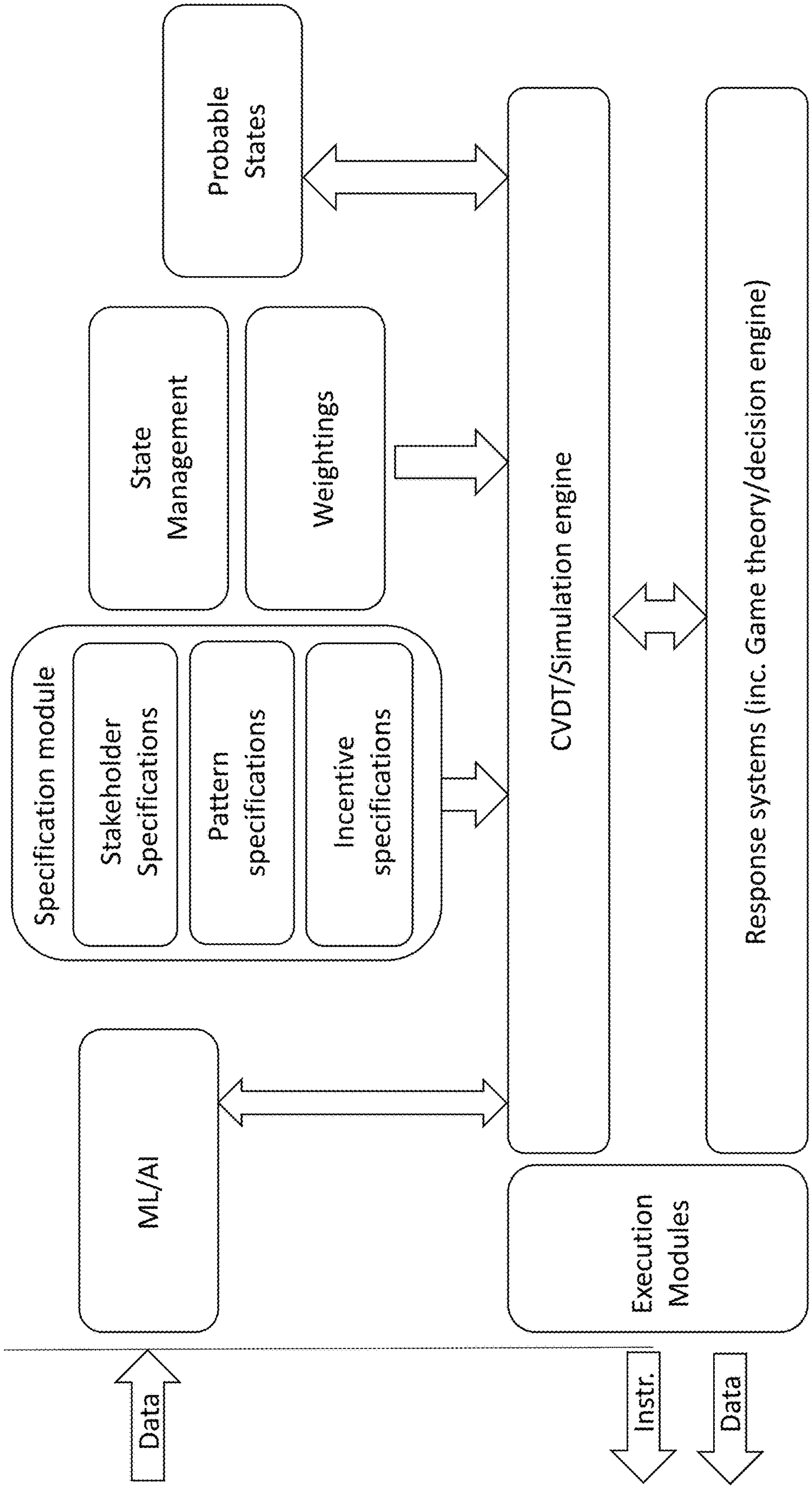

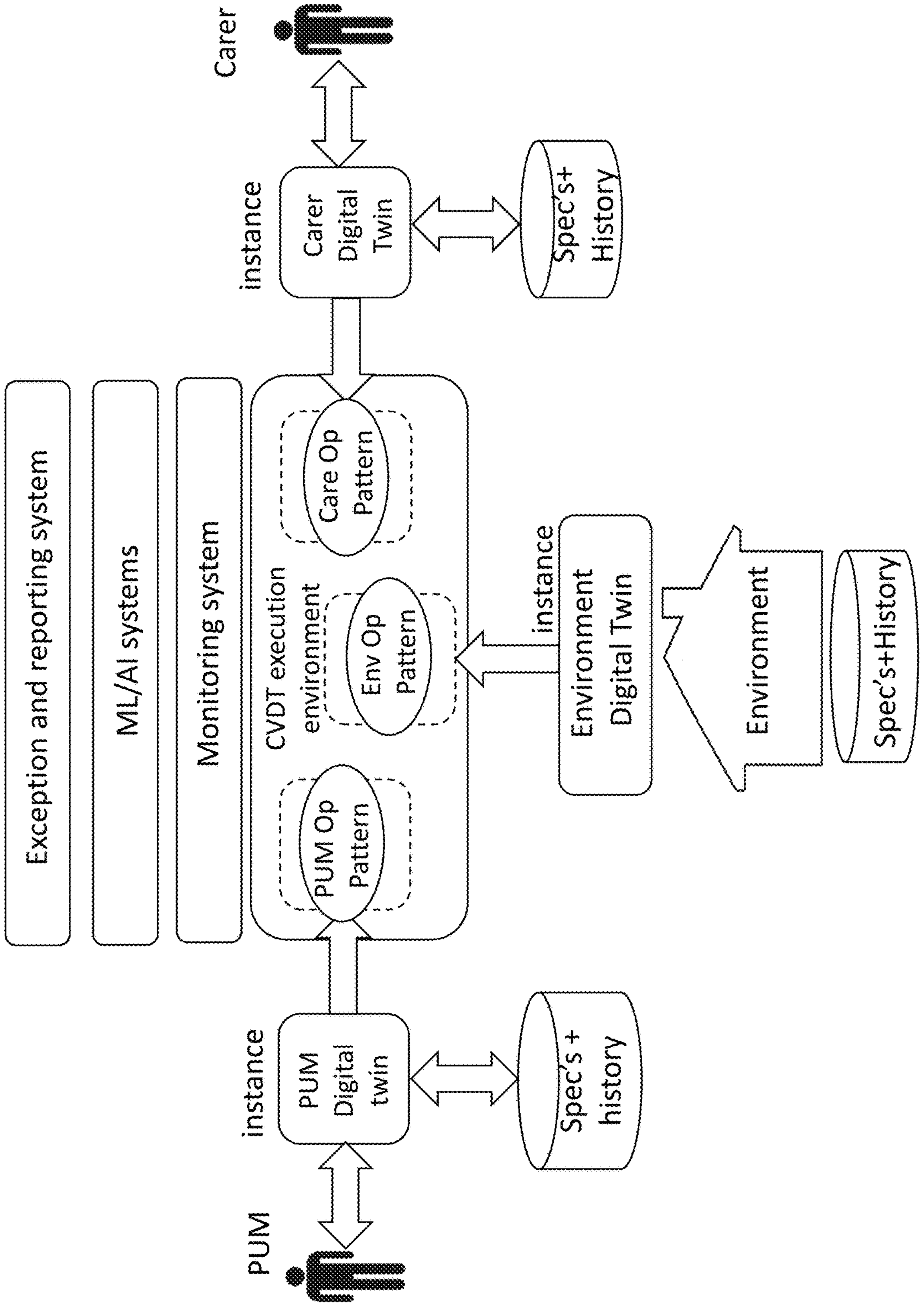
FIG. 16 CVDT environment

FIG. 17 CVDT pattern and response systems
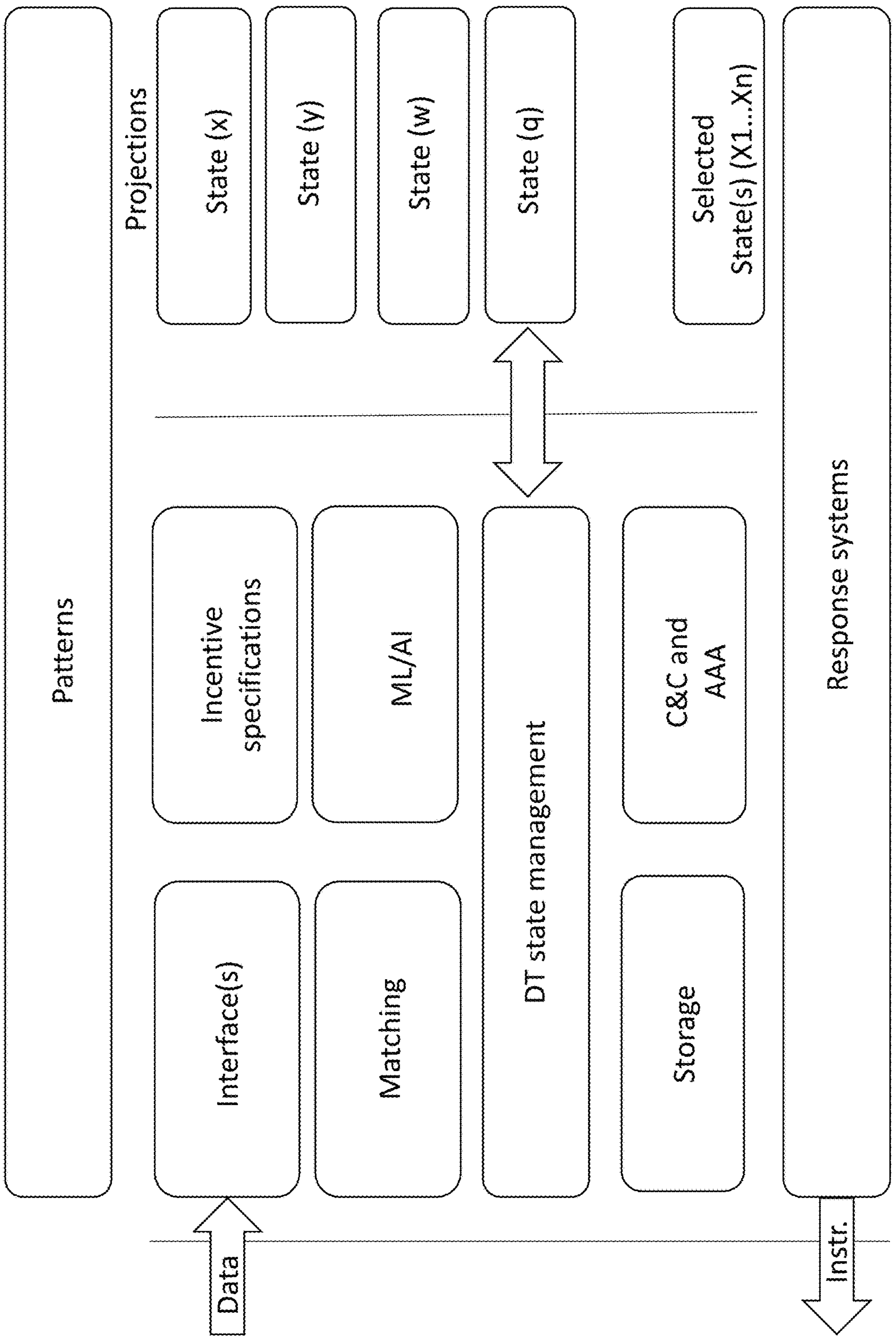

FIG. 18. CVT Response system
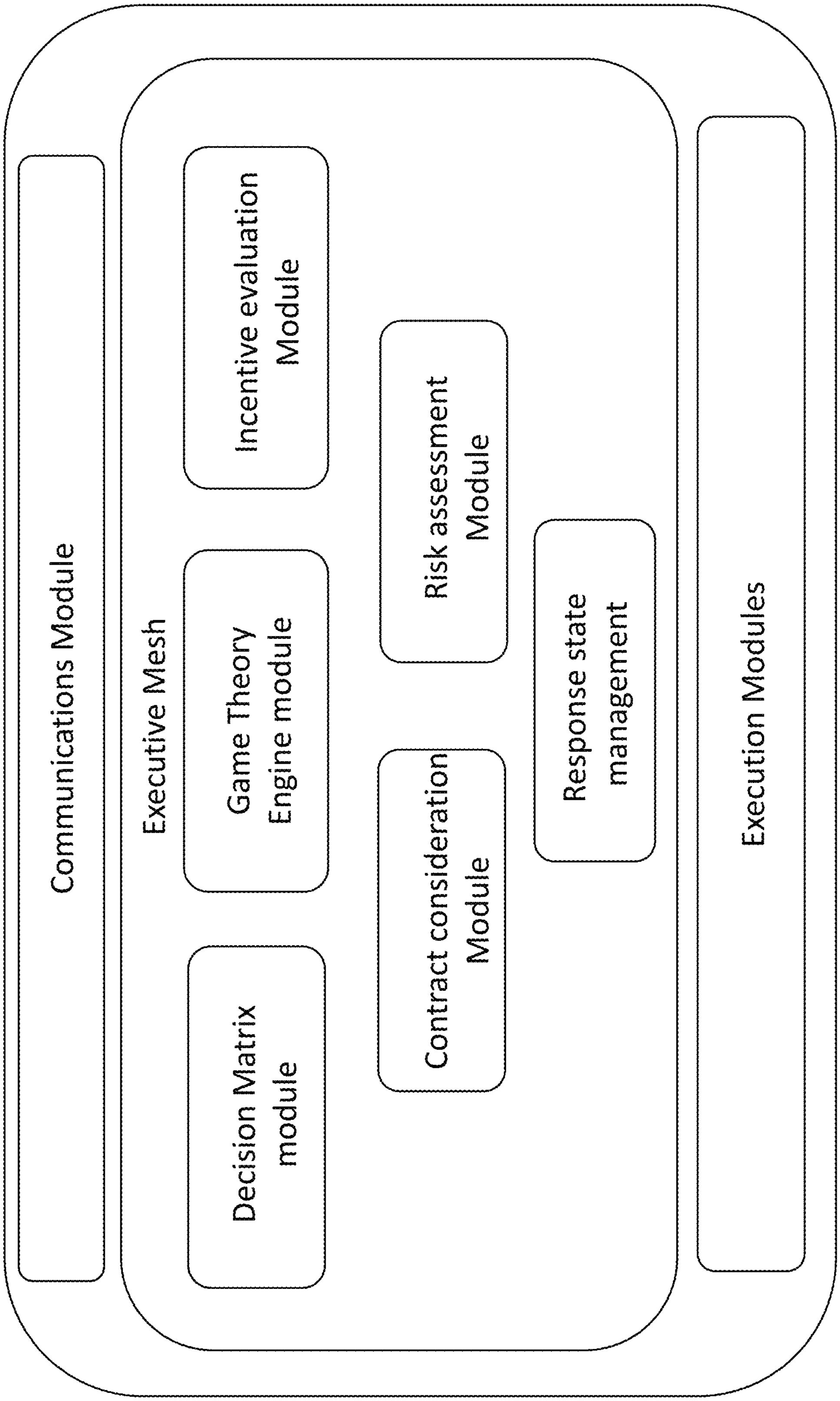

CARE VILLAGE DIGITAL TWIN SYSTEM AND METHOD

This application claims priority to U.S. Provisional Patent Application No. 63/385,592, filed on Nov. 30, 2022, and is incorporated by reference herein in its entirety.

BACKGROUND

Field of the Disclosure

Aspects of the disclosure relate in general to a system to monitor a person under care.

Description of the Related Art

In traditional infrastructure technology environments, Personal Emergency Response Systems (PERS), also known as Medical Emergency Response Systems, allow persons to call for help in an emergency by pushing a button.

One example system is a two-way voice communication pendant that allows a person to call for assistance anywhere around their home. Personal emergency response devices make aging in place and independent living a possibility for persons under care. The personal emergency response device allows a person to remain connected with loved ones and emergency services through an existing landline telephone.

SUMMARY

A system of entities is represented by digital twins. Each digital twin incorporates specifications of the capabilities of the entity. Each digital twin incorporates the physical characteristics of the entity. Each digital twin represents the state of the entity. The interactions between digital twins provide an accurate and timely representation of the interactions between the entities.

One aspect includes a system to monitor a person under care by a stakeholder. A transceiver receives a plurality of tokens from a plurality of environmental sensors configured to monitor the person under care. Each of the tokens comprises at least in part a detected data set representing behaviors of the person under care in an environment. Each of the behaviors is represented by a multi-dimensional feature set forming part of a health care profile for the person under care, wherein the token is encrypted using an encryption key. A non-transitory computer-readable storage medium stores a digital twin of the person under care. The digital twin comprises a dynamic tokenized representation of quiescent behaviors of the person under care in the environment. At least one processor analyzes the digital twin of the person under care instead of analyzing the plurality of tokens received from the plurality of environmental sensors until the at least one processor receives a token indicating that a wellness or care event has occurred. When the wellness or care event has occurred, the processor is configured to decode the plurality of tokens with the encryption key, analyze the plurality of tokens, and change a state of the plurality of environmental sensors or notify the stakeholder.

The at least one processor may be configured to identify potential future states of the person under care by analyzing the digital twin.

The at least one processor may be configured to identify potential future states of the person under care by analyzing the digital twin and the plurality of tokens.

The processor may use machine learning to analyze the digital twin and the plurality of tokens.

The encryption key may be unique to the person under care.

The changing the state of the plurality of environmental sensors may alter a monitoring focus of the environmental sensors.

The monitoring focus may increase the fidelity or granularity of the environmental sensors.

The detected data set may be from a breathing sensor, or heart-rate sensor.

The transceiver may transmit the token to a second care system.

The second care system may be determined based in part on the detected data set.

The care system may be determined based in part on the at least one stakeholder's relationship to the person under care.

The at least one stakeholder may be determined by data pertinent to the at least one stakeholder's relationship with the person under care.

Another aspect includes a method to monitor a person under care by a stakeholder. A transceiver receives a plurality of tokens from a plurality of environmental sensors configured to monitor the person under care. Each of the tokens comprises at least in part a detected data set representing behaviors of the person under care in an environment. Each of the behaviors is represented by a multi-dimensional feature set forming part of a health care profile for the person under care, wherein the token is encrypted using an encryption key. A non-transitory computer-readable storage medium stores a digital twin of the person under care. The digital twin comprises a dynamic tokenized representation of quiescent behaviors of the person under care in the environment. At least one processor analyzes the digital twin of the person under care instead of analyzing the plurality of tokens received until the at least one processor receives from the plurality of environmental sensors a token indicating that a wellness or care event has occurred. When the wellness or care event has occurred, the processor is configured to decode the plurality of tokens with the encryption key, analyze the plurality of tokens, and change a state of the plurality of environmental sensors or notify the stakeholder.

Another aspect includes anon-transitory computer-readable storage medium encoded with data and instructions. When executed by a processor the data and instructions cause a computing device to perform a method to monitor a person under care by a stakeholder. A transceiver receives a plurality of tokens from a plurality of environmental sensors configured to monitor the person under care. Each of the tokens comprises a detected data set representing behaviors of the person under care in an environment. Each of the behaviors is represented at least in part by a multi-dimensional feature set forming part of a health care profile for the person under care, wherein the token is encrypted using an encryption key. A non-transitory computer-readable storage medium stores a digital twin of the person under care. The digital twin comprises a dynamic tokenized representation of quiescent behaviors of the person under care in the environment. At least one processor analyzes the digital twin of the person under care instead of analyzing the plurality of tokens received from the plurality of environmental sensors until the at least one processor receives a token indicating that a wellness or care event has occurred. When the wellness or care event has occurred, the processor is configured to decode the plurality of tokens with the encryption key, analyze the plurality of tokens, and change a state of the plurality of environmental sensors or notify the stakeholder.

BRIEF DESCRIPTION OF THE DRAWINGS

To better understand the nature and advantages of the present disclosure, reference should be made to the following description and the accompanying figures. It is to be understood, however, that each of the figures is provided for the purpose of illustration only and is not intended as a definition of the limits of the scope of the present disclosure. Also, as a general rule, and unless it is evident to the contrary from the description, where elements in different figures use identical reference numbers, the elements are generally either identical or at least similar in function or purpose.

FIG. 1 is a block diagram of a Care Village Digital Twins (CVDT) execution environment.

FIG. 2 is a block diagram of a CVDT for a Stakeholder.

FIG. 3 is a block diagram of a Care Village Digital Twins for Device(s).

FIG. 4 is a block diagram of a Care Village Digital Twins for environments.

FIG. 5 is a block diagram of a Care Village Digital Twins at different times.

FIG. 6 is a block diagram of an alternate predicted Care Village Digital Twins.

FIG. 7 is a block diagram of an alternate and linear predicted Care Village Digital Twins.

FIG. 8 is a block diagram of predicted states of a person under monitoring (PUM).

FIG. 9 is a block diagram of predicted Care Village Digital Twins with configurations.

FIG. 10 is a block diagram of pattern identification, matching and creation systems.

FIG. 11 is a block diagram of a Care Village Digital Twins system.

FIG. 12 is a block diagram of a Care Village Digital Twins system.

FIG. 13 is a time diagram of Care Village Digital Twins predictions.

FIG. 14 is a diagram of Care Village Digital Twins analytics.

FIG. 15 is a diagram of Care Village Digital Twins simulations.

FIG. 16 is a block diagram of a Care Village Digital Twins environment.

FIG. 17 is a block diagram of a Care Village Digital Twins CVDT pattern and response systems.

FIG. 18 is a block diagram of a Care Village Digital Twins response system.

DETAILED DESCRIPTION

Aspects of the present disclosure include representation of physical entities, such as devices, sensors, stakeholders, environments and other entities may be undertaken by the creation of digital twins. These digital twins in the context of a care village are known as Care Village Digital Twins (CVDT). Each Care Village Digital Twins can provide a representation of the physical entity it represents, including specifications, configurations, state and any data that such an entity can generate in a specific context. This can include multiple sensors capable of providing comprehensive data sets, which can be represented by multiple Care Village Digital Twins arranged into a composite CVDT, so as to represent, for example an environment that includes devices, sensors, stakeholders and other entities in any arrangement.

A Care Village Digital Twin can represent the configuration of a sensor in an environment, such as a device, and can be in the form of a software simulation that mimics the configuration and operations of the sensor, such that when fed with the incoming data to that sensor, which may include and/or in whole or in part be based on a facsimile of that data, will accurately produce the output of the physical sensor. Such an arrangement may include feedback mechanisms such that with a known and predictable configuration and sensor operations and the use of the data generated by the sensor, the input to the sensor may be more accurately represented. This may also be the case when there are multiple sensors, which can capture the environment and context in similar or differing manners so as to more accurately capture the conditions of input to the at least one sensor.

The Care Village Digital Twins can in correlation to the actual sensor represent the state and configuration of the sensor and the data sets generated by that sensor. This ability to create, initialize, deploy and operate such Care Village Digital Twins of individual and groups of sensors provides a unique approach to the operations and management of these sensors, their configurations, the data sets they generate and the environment and context in which they reside.

Each stakeholder, device, system, infrastructure and other embodied elements of a care village can have at least one digital twin representing their state.

Such Care Village Digital Twins can then be updated continuously, periodically and/or on an event, trigger, alert or on other real time data and/or can be refreshed in alignment with any changes in the state of the embodied elements they represent.

One key aspect of this approach is avoidance of placing an unsustainable processing burden on the embodied elements operating within the care village, the management of the Care Village Digital Twin's representing those embodiments and the overall care village management, administration and/or reporting systems.

The state of each of the embodied elements, the data they generate and/or communicate and the representation of the state of the stakeholders generally is most often confidential and private to those stakeholders, the devices that are monitoring them and the systems and infrastructure enabling and supporting those activities.

The use by the system of tokens to facilitate data communications ameliorates these concerns to a large degree, however the system can also employ a series of vector representations of these tokens so as to, in part, avoid over burdensome and complicated key management of such tokenized data.

The use of a comprehensive set of digital twins for the prediction, detection and avoidance of misaligned incentives, rorts or other activities, behaviors and outcomes provides a unique approach to addressing such issues.

Care Village Digital Twins

In a care village each of the entities in the system can have a digital twin. This digital twin is a representation of that entity. These representations may initially be frameworks comprising a set of data representing that entity, which over time can be populated with data sets generated by for example, the care village systems, including from those entities, other sensors, behaviors, patterns and/or other data sources.

A Care Village Digital Twins can have state, in that each instance of a CVDT may represent a state of an entity that the Care Village Digital Twins represents. For example, a Care Village Digital Twin of a person under monitoring (PUM) is a representation of that PUM at a specific time (a specific time or period of time), where the data of the state of the PUM is integrated into the Care Village Digital Twin, providing that CVDT with a corresponding state.

When a Care Village Digital Twin receives data from a person under monitoring and their environment, such a Care Village Digital Twin may then correlate that data to the Health Care Profile (HCP) of the PUM and the patterns that are operating in those circumstances. This provides a current representation of the state of the PUM and environment.

For example, the state of the Care Village Digital Twins at a point in time is a snapshot of the person under monitoring, their environment and any relationships with stakeholders with whom they are currently interacting at that time. This snapshot can then be stored in a repository as a record of that state. This and further subsequent snapshots may then form a history, and in some embodiments such snapshots may be recorded on a regular schedule and/or may be triggered automatically or manually. These snapshots may form an audit trail and be recorded in at least one distributed ledger.

One advantage of the Care Village Digital Twins is the state, including a series of such states, can be used by at least one predictive technique to identify potential future states of, for example, a PUM and their environment. In this manner the determination of the configuration of the sensors, alerting of stakeholders, advance provisioning of resources and/or other activities may be undertaken. The determination of such actions may be undertaken by the system monitoring functions and/or may include manual intervention and/or assistance. For example, in some embodiments at least one machine learning technique may be deployed to create sets of specifications, including for example, configurations of sensors, messages to stakeholders and/or PUM and the like.

A Care Village Digital Twin may, for example, provide for multiple predictive alternatives to be instanced. For example, each of these instances, in themselves a CVDT, can represent an anticipated state of a person under monitoring and their environment. The systems monitoring functions may then compare these predicted outcomes to ascertain the most likely to occur, and then generate specifications that can be deployed when appropriate.

Such Care Village Digital Twins may, in some embodiments be compared with other Care Village Digital Twins that represent other PUM with similar or same HCP and/or similar patterns. In this manner the predicted outcome, as represented by a predictive Care Village Digital Twin, may be compared to an actual or historical outcome of a person under monitoring. This comparison may be used to inform systems that are evaluating a CVDT, and as such may then vary the predictive weightings and subsequent activities of the monitoring system in regard to that CVDT.

A Care Village Digital Twin may comprise multiple CVDT's of a set of physical entities, in any arrangement. This can include patterns of operations and/or behaviors of those entities. In the case of sensors or other configurable entities, this can include representations of those configurations such that the data sets produced by such an entity can be predicted and represented within the set of CVDT's.

In some embodiments, an environment Care Village Digital Twin may comprise a set of representations of the sensors that populate an environment within the context and representation of the physical environment. Each of the Care Village Digital Twins of such sensors may include specifications for their operations, such as for example, their performance parameters, such as sensitivity, capture rate, data format, other configuration parameters and the like. In this manner the Care Village Digital Twins may postulate a configuration of the sensor representation, which is the CVDT of the sensor, such that if an event that is part of the pattern being operated by the CVDT were to occur, that sensor would produce a data set that represents that event. This configuration is a proposed or postulated configuration and may differ from the current operating configurations of the sensor. This postulated data set in such a configuration, may then be compared to the actual data set being received by the physical sensor. Should the data set received from the sensor be insufficient to identify the event that the Care Village Digital Twin is predicting, then the configuration of the physical sensor may be varied to match the postulated configuration of the CVDT of the sensor. In this manner the CVDT may operate a number of configurations for a sensor and in some embodiments use a best fit algorithm to establish a configuration for a sensor that matches the event set that is predicted. Such an approach can be highly beneficial when an event has been detected from one sensor, for example a sharp increase in acceleration from, for example, a device worn by a PUM, which can then be confirmed or verified by another sensor in that environment.

A Care Village Digital Twin of a Person Under Monitoring (PUM)

In some embodiments, when a person to be monitored in the context of a care village is inducted into the village, they are assigned a system wide unique identity. There may be certain further data sets that then form part of their initial representation. These can include, for example:

Relationships—Other stakeholders with whom they have relationships (e.g., Doctor, Carer, Friends and family, neighbors, pharmacy, delivery services, other services and the like.)

Health Data—the initial health condition(s) that have initiated the need for monitoring represented by their Health Care Profile (HCP). This can include the existing and current health conditions and a set of parameters to be monitored.

Environment—their initial domicile whilst under monitoring and those other locations to which they regularly travel. This may also include location, health and care-related services nearby, as well as social, cultural and economic information associated with the location.

Care village sponsor—At least one entity that sponsors person under monitoring membership of care village (—e.g., financial, insurance, VA, Medicare etc.) and characteristics of support, including services available, responsibilities/liabilities, rules of care and other specifications.

This data set can form an initial framework for a digital twin of that person under monitoring, however as the PUM undergoes monitoring a range of data sets can populate the digital twin making it more representative of the state of the PUM. This improvement in data and accuracy can, at the same time, be used to enrich the PUM's profile data.

In some embodiments, a Care Village Digital Twins framework can include a Health Care Profile (HCP), representing the condition of the PUM for which monitoring is invoked. This can include, for example, the specific condition(s) and/or treatments that a PUM is undergoing. This HCP provides the care framework that is determined by the relevant health professionals.

As compliance with health data protections, including HIPAA and equivalents is often mandatory, such data can be stored in at least one repository that is complaint with such mandated protections.

Such Care Village Digital Twins may include health data, creating an HCP that provides the care framework that is determined by the relevant health professionals, a "health twin", which forms the basis for recording the health journey of a PUM and can be anonymized to form part of the care village health data set. The use of HCP and profiles for the initial context can form the basis of a set of touch points for the stakeholders and care village systems when interacting with the PUM.

When a Care Village Digital Twin is initialized the HCP and patterns thereof can be integrated into the CVDT, through reference and/or embedding. This creates an initial state for the CVDT and can include the at least one configuration for the at least one device, incorporating sensing capabilities. Such configurations may initially be used to establish the state of a person under monitoring, environment and any stakeholders. The initial operations of the configured devices, including any sensors, is to establish the relationship between the patterns deployed for the HCP and the state of the PUM in the environment as related to those patterns.

One aspect is to create the "at rest" state of the person under monitoring and environment, described as the quiescent state, which is the expected and actual behavior of the PUM and the environment under normal conditions within the context of the appropriate HCP.

Care Village Digital Twins of a Sensor

A care village sensor can have a digital twin. When the sensor is initialized the configuration and specifications of the sensor are recorded in a repository, along with the identity, location, stakeholder relationships, device and other sensor relationships and the appropriate management and processing systems of and for the sensor representing the environment and context of the sensor. This forms the initial Care Village Digital Twins for that sensor, into which when initialized the initial data set from the sensor is also recorded. This combination provides the CVDT with an initial quiescent state of the sensor and environment.

The Care Village Digital Twins of the sensor incorporates the capabilities of the sensor, the configuration of the sensor, including any alternative configurations and the data set of the sensor in its initial quiescent state and the environment in which the sensor is deployed.

The Care Village Digital Twins representing the sensor and the sensors relationship to the environment provides an initial data set from which any variations may be represented as changes in the initial state of the Care Village Digital Twins. These variations may be compared to patterns of expected data sets from a sensor, or set thereof, that are part of an environment. In some embodiments there may be multiple CVDT's which are created, based on the operating CVDT, that have inputs of data that represent differing patterns, which may then have differing configurations applied to determine different outputs.

One aspect of the Care Village Digital Twins for a sensor, or set thereof, is as a means for tracking the reliability of sensors, for example using byzantine algorithms. This can include analysis of sensor behaviors, for example expressed as metrics which combine the configuration and operation of the sensor and the data sets generated within an environment, for the detection of faults, inaccuracies and/or other variations in the data sets provided by the sensor This can include comparison of Care Village Digital Twins sensor operations with physical sensors, deployed in the environment and/or deployed in a manner so as to establish a reference for that sensor. This can be used to establish metrics for the reliability of sensor, which in turn may be used by CVDT to evaluate data sent by sensors and modify the operations of CVDT to maintain accurate alignment between physical sensors and CVDT.

Care Village Digital Twins of an Environment

An initial framework for an environment can be established using data provided by an environment owner and/or resident, for example a PUM domiciled at such an environment, digital representations of any architectural 2D or 3D plans, including the location of the environment and the locations within that environment of any features and fixtures, including for example power or other outlets, entrances and exits, furniture, facilities and any appliances as well as any health and wellness related equipment. This initial framework can be substantiated, in part or in whole, by physical sensing of the environment through the capabilities of the one or more at sensors deployed temporarily or permanently in such an environment.

One aspect is the overall context that a Care Village Digital Twins representing an environment is located within. This can include the physical location and consequently, for example, the weather and other environmental considerations, both static and dynamic. For example, if a weather event, such as a heatwave, heavy rain, tornado, hurricane and the like is predicted or experienced by an environment, the Care Village Digital Twins can represent these environmental changes, and in some embodiments, may be used to predict variations of intensity for such events. This can in turn inform response systems as to the likelihood of resources and actions required to ensure the wellness of a PUM in such an environment when such conditions occur.

A Care Village Digital Twin may have a metric of variance which is the representation of the delta between the observed real time entity that the Care Village Digital Twin represents and the state of that entity as represented by the Care Village Digital Twins. For example, this can include time data, such the elapsed time since the last update of the CVDT by the physical entity, the degree of variance on any set of data that such an entity can provide to the CVDT and/or the degree of accuracy, or any other attributes of such data, that an entity may provide. For example, if a sensor is monitoring a single environmental aspect, such as temperature, the time of measurement, degree of variance and confidence or accuracy of that data may be conveyed to the Care Village Digital Twins of that sensor as a variance metric. In a more complex example, such as a sensor that captures audio, the variance metric may comprise a calculated value for the degree of accuracy the sensor, either directly and/or in combination with a signal processing system determines for that data set.

As part of the initial configuration of a Care Village Digital Twins for an environment, the HCP for the person under monitoring is included. The HCP includes a set of patterns which represent the behaviors and activities of the PUM, including the quiescent states for those patterns. In this manner the overall quiescent state of the environment and PUM may be established within the patterns that are operating.

The Care Village Digital Twins may be replicated as instances of the CVDT representing the actual state of the environment, so as to represent potential changes in patterns. These differing patterns may be selected by a monitoring system as the most likely to occur based on the sensor data from the CVDT representing the actual state of the environment and PUM. These variations may then be considered by, for example, a machine learning system, so as to predict the most likely change in a pattern. Such an approach can include the use of game theory and machine leaning in combination to create a decision matrix of likely outcomes.

This can then be used to vary configurations of the sensors within any of the CVDT, including the one representing the actual environment and PUM.

In some embodiments data sets from the sensors, both the physical sensors and those represented in one or more Care Village Digital Twins, may use an accretion approach, such that as each data set varies, the overall trend is accreted over multiple time periods using multiple CVDT, so as to predict, with varying levels of certainty the relative likely hood of the data from the physical sensors matching that of the sensor represented by the one or more CVDT.

The integration of sensors and indicia that can be used by sensors, for example barcodes, painted or applied locational indicia, for example a circle, number, geometrical shape, arrow or other indicator of direction and the like, which can use visible or invisible materials can be included in the Care Village Digital Twins. In this manner the changes in the state of the CVDT may be accurately measured and calculated using the combination of sensors and indicia. For example, if a sensor is monitoring a line or other shape painted, using for example a material that is translucent at visible wavelengths and visible to infrared wavelengths, the motion of a PUM passing such a shape can be recorded. This is also the case for a pet, where for example the indicia are placed at a height above the threshold for a pet. Such an approach may be used for entry and exit points to different rooms within an abode, enabling the tracking of the movement of a PUM without reducing their privacy.

In some cases, the use of Care Village Digital Twins may predict the optimum placement of such indicia within an environment. These indicia may be serialized to create unique instances. These indicia may be applied to vehicles as well as outdoors.

The Care Village Digital Twins that represent the actual initial state of an environment and PUM, can be form a representation of the environment in a quiescent state, which is "at rest", to which other CVDT may be employed based on this initial state to represent the potential states of the environment and PUM in differing circumstances. These predicted CVDT may, in some embodiments, be used as a corpus for one or more machine learning techniques to identify the most likely future state for a PUM and environment, which can in turn inform one or more systems, including the configuration of sensors within that environment, including those worn by a PUM, of the likelihood of the predicted change in state.

Care Village Digital Twins of Stakeholders

Each stakeholder in a care village may have a Care Village Digital Twin. This includes people and organizations. For example, an insurer may have a CVDT that represents the policies of that insurer in regard to other stakeholders, including for example PUM and/or suppliers of goods and services to that insurer for provision, in whole or in part, directly or indirectly to, for example, a PUM.

Individuals as entities may have a Care Village Digital Twin that represents their operations and activities within the scope of the care village. For example, a PUM, that PUM's family, friends, neighbors and the like. Additionally, each of the individuals, for example a carer, may also have CVDT which is their representation for their interactions within the care village. In the case where the carer is contracted to a service organization for the provision of their skills to a PUM, that organization may also have a CVDT. In this example the interactions with the PUM can involve the CVDT of at least three entities, the PUM, one Carer and one Carer stakeholder organization. This can also include the CVDT of the environment, including one or more sensors and devices within that environment and any other CVDT of an entity that is involved with the PUM.

Although there can be potential complexities of a Care Village Digital Twin representing an organization as a whole, the CVDT of a stakeholder organization can comprise, for example, a set of stakeholders CVDT each of which has a counter party, in that the organization has a specific relationship with another care village stakeholder. For example, a PUM can have health insurance, which is instantiated as a contract, for example a smart contract, and as such the stakeholder organization may create a CVDT that embodies that contractual relationship and is personalized for the specific PUM. In this manner the relationship of the PUM CVDT and Stakeholder organization, for example insurance company, CVDT becomes a simple one to one relationship. The stakeholder organization CVDT may, for example, include similar relationships with the service providers for that PUM with which the stakeholder organization has a relationship for the provision of those services to that PUM.

As the trend continues towards personalized care, the use of individual Care Village Digital Twin relationships creates the opportunity to predict and evaluate potential future individualized outcomes for a PUM with differing sets of inputs, such as differing care regimes, prescriptions, patterns of behavior and the like.

The use of machine learning and other big data analytics may be invoked on these data sets to identify patterns, both for the individual and for classes of individuals. These patterns may then be applied to Care Village Digital Twins in a manner supporting prediction of possible future states of those CVDT, to determine potential outcomes and their impact on the wellness of a PUM.

One aspect of the use of Care Village Digital Twins in this manner is representation of the various entities and their touch points of their interactions. These touch points, considered as the points of interaction, may have metrics that express theses interactions, such that one embodiment of these interactions could be a graph, which can then be evaluated by one or more machine learning techniques, statistical analysis and the like for the prediction of the possible future interactions. Such an approach can include the declared and calculated incentives of the entities involved to ascertain the potential range of possible outcomes.

In some embodiments such touch points may be represented as a network, for example as a neural network. This can also include the use of constraint-based logic to determine which outcomes are most likely and/or represent the incentive sets of each of the stakeholders, separately and in aggregate.

In some embodiments, a Care Village Digital Twin can be configured as "high touch" sampling mode which is then monitored by system, such that when difference between the CVDT and the real environment and the entities and stakeholders therein, exceeds or approaches a threshold and/or includes an alert/event, a monitoring system is switched to the real environment. This can include changing configurations of the entities therein for higher granularity, increased sample rate, larger and more diverse data sets and the like.

In some embodiments, strategies for data gathering and/or sampling of a Care Village Digital Twin and/or the real environment, and the entities therein, may be determined by the use of game theory. This can include, for example the deployment of CVDT's which are specialized for the verification of compliance of the monitored entities, including for example the evaluation of the incentives of the stakeholders involved.

Care Village Digital Twins Interactions for Prediction

Each Care Village Digital Twins has a specification which can be embodied in an operating CVDT. For example, a Care Village Digital Twins may be instanced in a computing environment, based on the specification of that CVDT and such instance can then be operated in a temporal state that is the equivalent of the actual time in the real world, which is network or other reference time. However, the Care Village Digital Twins may also operate in accelerated time, where for example the CVDT instance operations are operated at multiples of the network or real time.

In this example, the Care Village Digital Twins may use patterns that represent the wellness state of a person under monitoring in the context of their HCP to accelerate the elapsed time, and for example using comparisons with other PUM with the same HCP, can be used to establish the future time range when a wellness event is more likely. This can lead to the CVDT proposing configuration variations to the sensors of the PUM in anticipation of such an event, so that any negative effects can be, as far as possible mitigated. This can include determination and selection of the most appropriate response for such a situation.

One aspect of this approach can be the provision of additional care resources, for example additional time or visits from a carer or alerting a neighbor or relative that a wellness event may be more likely so that they may check on or in more frequently on the person under monitoring. For example, a relative or other stakeholder, which has been delegated by the PUM as a proxy with, for example, elevated rights over the configuration of the at least one sensor in the PUM's environment, may undertake a more active monitoring role. This can include, for example that stakeholder having an application that can recognize certain aspects of the PUM behavior, for example image, audio or other sensing, and use care village systems to interpret those sensor data, such that the stakeholders providing the critical monitoring function at or near the time of a wellness event.

In some embodiments, monitoring of Care Village Digital Twins, either operating or simulated may be delegated to other systems, including for example environment sensing, signal processing, token evaluation, incentive misalignment or other general or specialized systems configured to monitor either real environments, including the entities therein and/or CVDT representing such environments. In this manner there may be specialized monitoring functions, which can include human interactions, which are optimized for particular monitoring capabilities.

The ability, by the care village systems, to instantiate multiple Care Village Digital Twins and operate these at various temporal rates provides a secure capability of determining, using for example, machine learning, the most likely outcomes for at least one of such CVDT. This can include those that represent devices, stakeholder, systems, infrastructure and the like.

One aspect of this approach is the determination, prediction, extrapolation and/or confirmation of the at least one touch point for each of the Care Village Digital Twins interacting with each other, either as an instance in a computing environment on a variable time base and/or as a representation of the actual situation in the real.

In some embodiments, there may be a root Care Village Digital Twin, which is the representation of the current state of a stakeholder, device, environment, person under monitoring and the like. The root CVDT may also have a specification which represents the state of the CVDT at rest, which is in a quiescent state.

There may then be multiple instances of that Care Village Digital Twins that are branched from the root using at least one algorithm for predicting the future state of each of these branched CVDT.

In some embodiments, differing input data may be applied to multiple identical Care Village Digital Twins instances, for example data from previous corresponding situations may be input to at least one CVDT, which using accelerated time, can then be used as the basis, at least in part, of prediction of the likely situation in the CVDT being monitored for a PUM in real time.

One of the aspects of this approach may be the deployment of evolutionary and genetic types of algorithms to create a set of Care Village Digital Twins with differing inputs and application of differing algorithms to create a set of possible situations, which can then be used, for example, as a corpus for at least one machine learning, weighting, predictive and/or other probabilistic technique, including for example Bayesian techniques, to identify the likely situations and outcomes for a PUM over various timescales.

These variances of at least one Care Village Digital Twins, for example, using differing behaviors, exhibited by at least one PUM with a similar HCP, may then be used, for example in combination with evolutionary algorithms, to identify and potentially monitor behavior likely to have at least one wellness event.

This can include, for example the instancing of multiple Care Village Digital Twins, where each such Care Village Digital Twins has at least one touch point, which is a point of interaction, with another CVDT. These touch points can then be represented, for example, by a graph or other nodal structure, including the use of manifolds or other topological representations such as Hilbert spaces and the like. In these configurations at least one machine learning technique may be applied to evaluate, determine and/or predict the interactions, in terms of their incentives, dynamics, behaviors and/or outcomes.

These nodal interactions can, in some embodiments, be represented as vectors, which can include multiple attributes and any meta data, and as such can be presented as graphic representations for both machine and human interpretation.

In the situation where the sensor data feed is limited and/or constrained, for example where battery or energy availability or communications capability is limited, a Care Village Digital Twin may, based on calculation and/or through lookup tables of previous similar data sets, create a more contiguous data set. This can include retrogressive data revision in light of, for example delayed data feeds, for example if a person under yqvcgvnre9 is in a vehicle between home and medical facility with limited or no communications capability.

The use of Care Village Digital Twins for predictions, including of data sets, state and/or interactions, can provide the capability to model, emulate and/or simulate the patterns of behaviors and data sets representing those patterns in any arrangement. This can include the relationships between multiple Care Village Digital Twins, such as a person under monitoring, a carer and a stakeholder organization, such that the interactions between the parties may be evaluated to determine those that, for example, have the minimal impact on the wellness of the PUM, or have the least negative impact on all of the parties involved.

Part of this evaluation is the determination and use of metrics, especially those expressing the profiles, contractual relationships and/or and incentives of the parties involved. In some embodiments, one aspect is the use incentive weightings in a Care Village Digital Twin to identify potential misalignments.

Each of these evaluation systems may include configurations that support the selection of one or more methods of evaluation, such that the relationship between incoming data the methods and techniques applied to that data for evaluation and the outcomes thereof may be determined and/or audited. Within this approach there also may be one or permission systems, such that a stakeholder may choose to opt in or out of one or more evaluations of data sets pertaining to their wellness and environment.

Digital Twins and Directed Learning/Supervised

Machine learning, a subfield of artificial intelligence, focuses on computer algorithms that use computational methods to "learn" information directly from data, without relying on predetermined equations, instruction sequences and/or similar deterministic specifications. Machine learning algorithms work in a way that allows them to improve their performance as the amount of data available for learning increases. A very common approach to implementing machine learning is through the use of artificial neural networks (ANN), which are computer systems that are designed to simulate the workings of the human brain by modeling the way neurons process and transmit information. A typical artificial neural network is made up of a number of nodes, or neurons, where each node takes multiple data inputs and produces a single data output that is a function of the summatory of the weighted inputs, and these nodes are interconnected, typically, in a layered topology, where the outputs of one layer of nodes are fed as inputs for the next layer of nodes. Artificial neural networks may have other topologies and the way each node combines its data inputs to generate a data output may vary as well.

Learning in an artificial neural networks-based machine learning system involves adjusting the weights applied to every input and the output threshold of every node in order to improve the results of the overall output of the network. Approaches to learning in these systems are usually categorized as supervised, unsupervised and reinforcement learning. Each method is best suited to a particular set of applications.

Supervised machine learning methods implement learning from data by providing relevant feedback. This feedback can be in the form of metadata, including, for example, labels or class indicators, which are assigned to input data sets. For example, an image of a person on the floor with a "fall" label assigned to it, or a combination of acceleration, altitude, and inclination sensor dataset with a label of "walking" assigned to it. Feedback can also be in the form of a function that maps input data to desired output values. The input data and the associated metadata or output mapping are known as training data. The goal of supervised machine learning is to build models that generalize from the training data to new, larger, datasets.

Supervised machine learning is well suited for use on classification, which refers to predicting discrete responses from the input data. For example, whether sensor dataset represents a PUM's fall, a step or other movement-related state of a PUM, whether a sequence of sounds represents a PUM calling for help, and/or whether a combination of risk factors for the PUM should result in a call to an emergency medical service and/or the like.

Supervised machine learning is also used on regression applications, where the system predicts continuous responses from input datasets. For example, in some embodiments a supervised machine learning system can be used for estimating physical quantities such as room temperature, acting as a virtual sensor based on historical temperature data, which can be used, for example, to provide missing data from real sensors that stop working or communicating under some circumstances. This approach can also be used in other embodiments to generate simulated sensor input to a sensor, device and/or environment Care Village Digital Twins, modeling a real-life behavior and/or situation for the CVDT.

In some embodiments the selection and deployment of a Care Village Digital Twin or set thereof may be determined, at least in part, to simulate or model particular behaviors and ascertain predictive traits using machine learning in a directed manner. This can include the use of one or more frameworks for establishing outcomes based on the determined variations of the Care Village Digital Twins configurations. For example, there may be specifications of the degree of permissible variation in differing contexts for a given/desired/intended/predicted outcome (inc. sets thereof). This can include system derived pattern detections for outcomes that indicate compliance variations which are in whole or in part determined through the use of machine learning techniques.

Digital Twins and Undirected Learning/Unsupervised unsupervised

Unsupervised machine learning methods, on the other hand, do not require any labeled training data. Instead, they rely on the data itself to identify patterns and relationships. These methods are useful for identifying hidden patterns and/or intrinsic structures in the input data. Unsupervised machine learning is used to cluster data points together, based on common characteristic. For example, identifying the pixels and/or other elements of an image that belong to an object or a person, in image recognition applications, or to find groups of sensor signals, or patterns, which are most likely to be present for a specific PUM situation. Clustering based on unsupervised machine learning systems can also be used in some embodiments to identify outliers. For example, when a sensor dataset pattern falls outside of a normal situation, which in some cases may indicate an emergency situation or a faulty sensor.

Machine learning-based clustering can also be used in some embodiments to identify patterns within a Care Village Digital Twin that lead to a specific type of outcome. For example, such system can be used to identify associations between different combinations of datasets representing sensor inputs, PUM's states, actions and/or environment states with desired outcomes (a fall or another emergency is avoided, an emergency response happens on time, etc.) or undesired outcomes (an emergency situation occurs, resources to respond are not ready on time, notifications are not provided on time, etc.).

Another classification of machine learning methods is reinforcement learning, which, as with supervised machine learning, uses feedback mechanisms. In reinforcement learning, however, the feedback is presented in the form of a general reward value for the generated output, instead of a set of the correct output dataset. The machine learning model is usually trained with a series of trial-and-error repetitions until it is able to resolve each case correctly. This approach is useful for training systems to make decisions to achieve a desired goal in an uncertain environment. In some embodiments this machine learning method can be combined with one or more Care Village Digital Twins, where the Care Village Digital Twin is run multiple times and the machine learning system gets trained to generate the appropriate response, in the form of a decision dataset, to achieve the desired outcome for a PUM.

The combination of machine learning and game theory can provide the identification and deployment of games that are representative of the characteristics and behaviors of stakeholders and other entities in environments. This can be particularly useful when monitoring, for the detection of data inconsistencies, contradictory data sets, out of band data and/or insider self-serving interests and the like.

One aspect of this approach is identifying the real or potential unintended circumstances, behaviors and/or outcomes, where for example reconciliation of the data sets provided by the one or more entities and the machine learning generated data sets, both potentially represented by one or more Care Village Digital Twins, can give rise to evaluations and reconciliations that identify such circumstances, behaviors or outcomes.

One application of directed machine learning is identification of derivations and construction of new patterns derived from system data sets, such as those represented by operating and simulated CVDT, that match one or more characteristics of the context and PUM behavior variations.

Example Embodiment

A Care Village Digital Twin can be instantiated as a set of specifications analogous to a class, which when an appropriate operating environment is deployed, becomes an operating CVDT with state. A Care Village Digital Twin includes specifications that represent a physical entity, such as a device, sensor, stakeholder, environment and the like. These specifications include both the definitional capabilities of the entity and the configuration of the entity. For example, a device may have definitional specifications of that device's capabilities, for example a temperature gauge, a camera with specific focus and resolution and the like. In the case of a stakeholder this may include, for example, the role of the stakeholder. Each of the entities may then have configuration specifications, if the entity supports such configuration. For example, a camera may have adjustable resolution and/or focus, a device that includes multiple sensors may have the ability to increase or decrease the sensitivity of each sensor and the like. In the case of a stakeholder the configuration specifications may include their availability and/or times of work, rates of cost, technical capabilities and the like.

Once the Care Village Digital Twin has been instantiated by deploying the supporting operating environment, each of the entities represented by the CVDT has a state, determined at least in part by the configuration of that entity, represented by the CVDT. This is the operating CVDT.

The Care Village Digital Twin includes the relationships between the entities represented by that CVDT. In a simple example the CVDT may have two entities represented, a device and a stakeholder (for example a PUM). In this example the device is being worn by the PUM, and comprises three sensors, an accelerometer, a gyroscope and an altimeter, each of which has definitional and configuration specifications. The Care Village Digital Twin has an expressed relationship between the device and the stakeholder, in that the device is being worn and is providing a set of data as to the state of the device and the sensors therein. This data represents the state of the device and wearer and may form a pattern expressed as a set of inputs, data from the device, and a set of outputs. This pattern may be deployed within the CVDT as further specifications and/or can be deployed in a system that is monitoring the CVDT, for example a signal processing system. In either case if the data set varies in a manner that ceases to match the specifications including parameters, thresholds, tolerances and the like, that are incorporated within the operating pattern, including those managed by a system monitoring the pattern, one or more response systems may be invoked to undertake an action, declare an event, provide one or more configuration specifications to one or more sensors and/or the CVDT that represent those entities, and the like, so as to provide an effective response, potentially using a decision matrix, to those data set variations.

The state of the Care Village Digital Twin representing those entities may be adapted in line with that data, through for example changes in configuration of those entities and the like.

This can include invoking new patterns that represent the data from the entities, and/or can involve invoking further Care Village Digital Twins into an operational state and/or can involve adding further entities to the operating CVDT in any arrangement.

Execution Environment

A care village operating environment capable of supporting the instantiation of Care Village Digital Twin specifications into operating CVDT's includes a set of general operating system capabilities, such as processing, preemptive scheduling, threading (including single and multithreading), storage, persistence and repository capabilities, for example a data management system, and other standard capabilities in the form of libraries and modules. This can include a set of engines which incorporate specific sets of functionalities, such as for example a physics engine, where such an engine may be invoked and supplied, for example though an API and/or through a messaging system, which for example, may be secure, with data sets from a Care Village Digital Twin representing a set of devices, sensors, stakeholders and/or environments. Such an engine may then apply the specific operations, such as providing a model of real-world physics, so as to provide an output to another system, representing the physical outcomes of the real world. The operating environment may include a set of specialized engines, in any arrangement, that encompass aspects of the physical world which the CVDT represents, for example this may include health engines, stakeholder engines, where for example this may include stakeholders who are organizations, where certain logic and processing may be undertaken on behalf of the organizational stakeholder, CVDT prediction and simulation engines and the like.

The operating environment may be instantiated in whole or in part, for example a subset of the functionality may be part of, for example, a device which incorporates a set of sensors, and can provide a minimal level of support for a Care Village Digital Twin representing at least one of the sensors. In this example the operating environment may include communications capabilities to enable the data from the Care Village Digital Twin and/or sensor to be securely provided to another CVDT that, for example includes the device based CVDT as well as a set of other CVDT. For example, such a Care Village Digital Twin may incorporate CVDT from this device and a further set of sensors that a are monitoring a PUM in an environment.

The operating support environment can be distributed, including edge computing embodiments, and can include the use of cloud-based systems, including for example, containers, serverless and other similar cloud based scalable deployment embodiments.

The operating support environment can include a Care Village Digital Twin engine which provides a set of capabilities that support prediction, simulation, and other machine learning based techniques that can be based on specification and inputs from an operating CVDT. This engine may be invoked by one or more systems, such as for example a monitoring system, to create one or more Care Village Digital Twins that replicate the operating CVDT with differing inputs, configuration specifications and consequently differing outputs. These variations may then be considered by further systems to establish potential trends, vectors and/or other potential outcomes that may affect the wellness of the PUM represented in the operating CVDT. Each of these derived CVDT, that include one or more variations from the operating Care Village Digital Twin may be configured to run at an accelerated rate, so as to determine an outcome based on the changes to the inputs. These results may then be compared to other derived CVDT outputs with differing inputs and to a direct copy the original operating CVDT to determine a set of possible outcomes, which can then be evaluated to ascertain the probability of such outputs based on the data sets. In some circumstances, the configuration of the sensors represented by the operating Care Village Digital Twin may be varied, so as to more accurately determine whether a particular predicted wellness event has or is likely to occur. For example, a camera may be configured to operate to detect movement within a specific timeframe, as the prediction, based on the data set of the operating CVDT and the evaluated outcomes of the predictive CVDT, indicate that the probability of a wellness event is likely, for example, the PUM may experience dizziness when standing from sitting, which could lead to a fall.

This ability to invoke multiple versions of an operating Care Village Digital Twin, including one or more direct copies, supports the prediction and evaluation of potential wellness events without intervention of the physical PUM and their environment. This approach can be used to provide necessary resources, including the predictive scheduling of those resources, based on the likelihood of the PUM having a wellness event.

The data sets created during this process may then be used as part of a corpus for training machine learning and AI systems, where the results, including the wellness events occurring or not, can be included, so as to improve the overall accuracy of the predictive techniques.

The use of multiple Care Village Digital Twins can include multiple branches of CVDT with differing inputs leading to differing outputs which can then be provided to one or more response systems, including one or more decision matrix, where the responses are evaluated by one or more evaluation systems. Theses response sets can be evaluated for their potential effectiveness in responding to the wellness of the PUM, using for example machine learning and/or other automatic processes as well as human evaluation, for the purpose of determining the optimal response to the situation.

In this manner the considerations of the possible alternatives that offer the PUM an outcome which optimizes their wellness and well-being may be invoked. This provides a beneficial advantage over fixed rule-based systems, which are often rigid and determinative providing insufficient effective, flexible and optimal responses.

Detect a consistent variation based on operating CVDT data, such as when a person experiences momentary dizziness, detected as arbitrary head movement, on an increasing basis, that subsequently leads to a fall or other wellness event, then this variation, which the further CVDT predicted, is then formalized as a pattern for operating CVDT. In this manner the range of potential situations that may affect a PUM is captured and persisted in manner that can then be distributed to other PUM with similar condition and becomes part of the set of patterns that are used in the process of monitoring.

In some embodiments, the operating support environment may include a stakeholder engine. This engine can provide capabilities for the interpretation and execution of specifications, for example those in the form of a contract or other structured format, such that based on the input received by the specification engine and the processing of the specifications presented to and/or held by that engine, the engine will generate an output, which can comprise data, further specifications and/or configurations or other instructions for other of the operating support environment and/or the CVDT and other entities interacting with such an environment.

The specifics of the specifications will be dependent on the stakeholder, in that for example, a PUM or carer may have specifications representing, in the case of the PUM, their preferences, incentives and/or constraints and for a carer, for example a similar set of specifications, such as their availability, work hours or other determinative factors representing their current capabilities in the care village domain.

In the example where the stakeholder is an organization, the specifications may include the contractual relationship between the organization, for example an insurance company and a PUM.

Such specifications may be in the form of smart contracts, where the relationship between the stakeholder engine, the smart contract and the distributed ledger is such that the processing of the specifications is protected, for example using a protected processing environment, and secure ensuring a chain of custody and control such that the processing of such contracts supports the immutable recordation of the distributed ledger.

Stakeholder organization engine can be used to simulate potential stakeholder responses based on procedural specifications, for example, those held in a contract between the parties, including for example, a smart contract, and as such this data may be used in one or more response system evaluations to determine the optimum outcome for a PUM and/or the other counterparty stakeholder.

The general operating environment, through provisioning of physics engine and stakeholder engines and the capabilities of the operating environment can enable simulations, for example those that may be invoked by a CVDT engine. This can include single and multiparty simulations where a series of projected states and outcomes may be simulated. This can include a hybrid of real outcomes and simulated outcomes in any arrangement. Both real and simulated outcomes may be based, in whole or in part, on stored data sets that have been accrued from other stakeholders and environments that have sufficient similarity to the simulation being currently undertaken. In this manner, data from a previous situation that involves a PUM with a similar condition, HCP and operating pattern in an environment that is similar to the current situation being simulated may be used to evaluate potential outcomes.

In some embodiments the simulations may be provide data sets that are tested for compliance with one or more specification sets and CVDT representing those sets so as to evaluate any variations. For example, establishing that a PUM cannot be in two different locations simultaneously. Further compliance considerations may in the form of constraints such as when a PUM uses a particular pharmaceutical, the effect of that pharmaceutical is specified in the simulation, so as to identify the effect of an overdose.

One aspect of such simulations is the representation of relationships between the entities, including the stakeholders. For example, a fixed sensor can only be in a single location and consequently has a set of relationships with other collocated entities.

Response Systems

Care Village Digital Twin supported by an execution environment and the engines and modules thereof, can produce data sets that are specifications that are candidates for deployment in an operating CVDT, representing a physical environment including the stakeholders therein and/or may be supplied directly to the sensors, devices, communications and other system operating in the environment represented by the CVDT.

In some embodiments such data sets can be passed to a response system. A response system includes a set of modules which may respond to and operate upon that data. A response system may include a decision support system, for example a decision matrix.

The response system outcomes may be passed to one or more execution modules that can operate to undertake any variations in the configuration of the systems and manage any dependencies, scheduling, prioritization or other process handling.

The execution module may output a specification to the active operating Care Village Digital Twin for deployment in the physical environment and/or may output a specification to one or more CVDT to simulate the impact of that output specification on the actual operating CVDT and the entities represented by that Care Village Digital Twin.

In some embodiments, the response system may include the following modules:

Communications module: The communications module provides one or more API capable of communication with CVDT, so as to enable communications with CVDT and/or systems operating on behalf of and/or in conjunction with those CVDT. A primary function of the communications systems is to receive and transmit data sets from and to a CVDT. The communications module may also be invoked by an execution module to transfer data from the execution module to a CVDT.

Executive Mesh: The response system may include an executive capability in the form of an executive mesh that includes a set of modules that can be configured and operated in any arrangement.

The executive mesh involves logic processing that determines, in whole or in part what data sets the response system may provide to the operating CVDT and/or directly to the environment represented by that CVDT. The executive includes a set of modules, which can evaluate the data sets received and generate an output. This can involve requesting instantiation of further CVDT with differing data and may include state monitoring, so that outputs of CVDT may be provided to any module in any arrangement.

The executive mesh may include an operating environment that supports the processing of the executive mesh operations, including for example, transitory and persistent storage, memory, processing units, machine learning systems and other general operating support systems. In some embodiments this can include the execution environment described herein.

Executive mesh operations may, in part or in whole, use patterns, where those patterns are sets of specifications that include configurations and/or operations of the modules managed by the executive. For example, the executive may evaluate an incoming data set for one or more CVDT through comparison to an existing data set as part of a pattern and execute a series of configurations and instructions to the modules managed by that executive based on that comparison's outcome.

In some embodiments, these modules include:

Decision Matrix.

Game Theory Module (GTM)

Contract Consideration Module

Incentive Evaluation Module

Risk Assessment Module

Care Village Digital Twins and Vector Token

The decision matrix, in some embodiments, may be embodied as a graph system, lattice or other formalized decision structure. For example, a multi-dimensional lattice may be used to select the appropriate data set to be passed from the decision matrix to another module. The decision matrix may embody one or more patterns of outcomes, such that the traversal of the decision matrix leads to a consistent result in light of the input data. In some cases, these deterministic outcomes may be modified as further data becomes available, for example where additional CVDT of other entities, for example sensors, becomes available.

The game theory module (GTM) may employ a set of games to determine the likely and appropriate outcomes for the incoming data sets, so as to generate an outcome which may be passed to one or more modules.

In some embodiments these games may be consistent with other care village games that are used, for example, to identify misaligned incentives. The GTM may include games that have been identified through the observation and evaluation of the actions of one or more stakeholders within the care village.

The GTM can operate in conjunction with the other system modules, under the direction of the executive, to determine the appropriate games to be deployed and the associated hierarchies and selections of such games. This can include games deployed in one or more CVDT, including those that have been instantiated by the executive mesh, which can include selections to be deployed for one or more machine learning techniques, either for training and/or operational deployment.

The executive mesh may invoke one or more games to be deployed in any arrangement for the differing circumstances and interactions, representing interactions between stakeholders, systems, devices, sensors and other care village entities, which can include, cooperative and non-cooperative games, normal form and extensible form games, simultaneous and sequential move games, constant sum, zero sum and non-zero-sum games and symmetric and asymmetric games, and the like.

In some embodiment there may be contractual arrangements, expressed for example as specifications, including smart contracts that employ programmatic logic. These specifications may be evaluated, through for example, matching and comparison systems. This evaluation of the contracts under consideration can determine the appropriate data set that can be provided to one or more other modules.

In some embodiments the contract may comprise a set of conditions for the provision of a service, product or interaction, where the contract may represent the predicates required before an event or action can take place. The executive mesh may have certain contractual specifications that determine the operation of the care village systems. These specifications may be arranged in a hierarchy or priority framework, such that if the conditions represented by the data from a set of CVDT represent a specifically identified condition, then the executive mesh may operate to make an action in response to those specific conditions, through the one or more execution modules. For example, this would be the case when a PUM is undergoing a life-threatening event, and as such the executive mesh would contact 911.

In some embodiments there can be a set of incentives that each of the stakeholders has declared and/or the system has calculated. These incentives can be used, in whole or in part to determine the weightings or other values for a set of data and/or can be represented as a set of data that can be provided to one or more other modules.

In some circumstances the incentives may be used to vary one or more CVDT configurations so that the executive may gain additional data sets for the executive processing.

In some embodiments there may be a risk assessment module which has a set of patterns, expressed as specifications, which are representative of the risks posed to a stakeholder in their environment. This can include data based on the, for example HCP and/or operating pattern of a PUM. The data sets created by this module may be provided to one or more other modules.

For example, the risk assessment module may involve consideration of a range of specifications, such as stakeholder well-being, economics, contractual commitments, service and/or product availability and the like. In some embodiments there may be contradictory specifications from differing stakeholders that the executive mesh may reconcile and/or evaluate the outputs of such specifications in one or more CVDT that are instantiated for that purpose.

This can include new models for payment, such as usage-based insurance and the like.

In some embodiments these modules of the executive mesh may be arranged in a matrix, such that each module may provide input to any other module and each module may receive output from any other module. The executive may then, using any of the modules, select the appropriate data sets to be communicated to one or more execution modules.

Each of these modules may be invoked by the executive module to provide to that module and/or to other modules one or more data sets. The executive module may then, using either fixed or variable logic, pass a resulting data set to one or more execution modules for onward transmission to one or more end points.

The execution module communicates the data to the appropriate end point and manages the state of that end point, including any dependencies. The communication includes an acknowledgement capability, such that although the communications may be asynchronous, the state of the end point is maintained by the execution module. This state can be reported to the executive module for maintenance of the overall state of the system.

One aspect of the executive module is the capability to support multiple, potentially contradictory data sets simultaneously. These data sets can be compared to ascertain, within any constraints of the execution environment, for example the physics engine, the range of data sets to be sent to execution modules. For example, this can include data sets that configure sensors in an environment so as to obtain further data sets that can support or contradict the data set under consideration.

This evaluation may include the use of machine learning techniques, such as deep learning, neural networks, regression modelling and the like. The executive may produce a set of candidate data, and then, in some embodiments provide such data to one of the modules of the executive, for example, this data may be provided as input to the game theory module, incentive module and/or risk assessment module, each of which may then produce further data sets for evaluation by the executive module.

A further aspect is the use of simulations systems using Care Village Digital Twins, where such a simulation may provide a data set that represents an intervention. For example, these can be configured as CVDT sponsored, suggested, initiated interventions, which in turn can lead to predictions of outcomes based on differing interventions. In some embodiments, there may be configurable Interventions based on these predictions which can be applied to operating CVDT.

This intervention may be passed to the response system, where based on the operations of the executive, this intervention may be passed to an execution module for onward transmission to an operating CVDT and/or the environment represented by that CVDT. This can include creating sets of possible interventions to ascertain appropriate actions though invoking one or more CVDT. For example, this can include changing the configuration of a CVDT representing an HVAC system in an environment, so as to assess the outcome for the environment and the stakeholders therein.

In some embodiments, systems such as the response systems, Care Village Digital Twin management system and/or other care village systems may evaluate the costs-benefit, cost-value or other sets of action and outcome relationships. This can include differing perspectives, such as wellness, stress, ease or effort expenditure, economic or financial and the like from the perspective of one or more stakeholders. This can include evaluation, through the use of multiple CVDT of the state changes and their actual and/or potential outcomes based on these evaluations. This can result in contradictory potential configurations or other changes to the operating CVDT, which can then be reviewed by care village systems, including through the use of machine learning and/or human intervention.

One challenge of a set of sensors that are operating, potentially on a 24/7/365 basis, is the ability of those sensors to generate sets of data, which can be continuous. This is exacerbated, as in many situations there are multiple sensors, such as those in devices with multiple sensors, which are capable of producing a total volume of data that can either require very significant processing power to evaluate that data. One approach to this stream of data, is the use of sampling on a periodic basis to alleviate that processing burden. Additional strategies deployed to manage this data flow include the use of evaluation of the data feed at the edge of the network to identify events of actions that can then trigger the data stream. Each of these approaches has various limitations, including battery life, missing crucial data, reliance on capabilities of the device for processing, lack of accuracy or granularity, privacy and security and the like. In some situations, a periodic approach is often used, where the data is sampled on a fixed periodic basis, such basis having been determined as appropriate for the situation.

Each of these approaches has some limitations, not least of which is the availability of the raw data feed to another device and/or system or a concatenated version of that data being available to another device and/or system.

The use of edge processing, such as image recognition and the like is generally constrained by the processing capability of the device at the edge, and as such if the raw data is made available to a processing capability and supporting systems with significantly more capability, the degree to which that data may be evaluated can be significantly enhanced. For example, time of evaluation, granularity, comparisons, identification of triggers, integration of additional data and the like.

To address this issue of deployment of the appropriate processing and evaluation techniques at the time required, each of the edge devices can be enabled to, and/or can be configured so as to, use a vector simplification of the state of that sensor and/or device.

In some embodiments, this can include a set of vectors that represent the interactions between entities, such as sensors and devices, where such a set may be represented by one or more tokens in any arrangement.

The vector may be represented as a token so as to enable the efficient distribution, management and use of the token by the at least one system element, including signal processing, devices and/or sensors, repositories and/or other care village system elements.

The vector is a simplification of the data, which is represented by a token, such vector indicating a trajectory of the data set in relation to the quiescent state of the sensor.

In some embodiments, the dynamics of an operating pattern, for example represented as vectors expressed as tokens generated by sensors, may be evaluated within boundaries of dynamic thresholds. For example, such boundaries may be used in determining which pattern, including sets thereof, is operating and/or is to become operating or dormant. Vector analysis may use support vector machines to establish the relevant hyperplane that represents at least one decision boundary. These boundaries may be adaptive and responsive to the set of vectors under evaluation.

In some embodiments, a Care Village Digital Twin may have a set of vectors that represent that CVDT, specifically the trajectory of the simulated or actual sensor data sets. These vectors may be passed as tokens, which are cryptographically secured to one or more other authorized and authenticated services. Such tokens may incorporate identifying characteristics of the sensors, devices, environments and the one or more CVDT that incorporate or reference these, such that this identification can provide sufficient data as to the operations by the one or more systems, which have been undertaken on those entities.

In some embodiments, there may be one or more vector evaluation systems, such as support vector machines, which operate as part of the execution support environment. For example, this can include evaluation of a vector by one or more monitoring system, which may require access to the data in the token and/or the configuration of the at least one sensor providing the data For example, in some embodiments, signal processing systems may receive multiple inputs from multiple sources (devices/sensors) and be configured to evaluate combination of vectors from multiple sensors/devices, which can be represented as patterns. These patterns may then be represented by further vectors expressed as tokens for further communications and evaluation.

These relationships of vectors and patterns may provide a lead indicator of change of state of an entity, including sensors, devices, environments, stakeholders and the like, enabling simplification of evaluation processing and representation of state of pattern and behaviors. This can include the configuration of multiple sensors so as to increase the data accuracy by evaluating multiple sensor data sets to ascertain and/or confirm accuracy of these data sets. For example, graphs and other nodal arrangements may be employed for both vectors and data sets in any arrangement.

In some embodiments, an entity, such as a sensor or device, generating the raw data may then incorporate the capability to represent that data as a token that incorporates one or more vectors.

The previous description of the embodiments is provided to enable any person skilled in the art to practice the disclosure. Thus, the present disclosure is not intended to be limited to the embodiments shown herein but is to be accorded the widest scope consistent with the principles and features disclosed herein.

What is claimed is:

1. A system to monitor a person under care by a stakeholder, comprising:

a transceiver configured to receive a plurality of tokens from a plurality of environmental sensors configured to monitor the person under care in a physical environment, each of the tokens comprising at least in part a detected data set representing behaviors of the person under care in the environment, each of the behaviors being represented by a multi-dimensional feature set forming part of a health care profile for the person under care, wherein the token is encrypted using an encryption key;

a non-transitory computer-readable storage medium configured to store a digital twin of the person under care, the digital twin comprising a dynamic tokenized representation of quiescent behaviors of the person under care in the environment;

at least one processor configured using a predictive technique and the digital twin of the person under care, to generate a simulated future state of the person under care and the environment, and, based on the simulated future state, determine whether a current configuration of the plurality of environmental sensors is sufficient to detect an occurrence of a predicted wellness or care event based on the simulated future state; and in response to determining that the current configuration of the plurality of environmental sensors is not sufficient to detect the actual occurrence of the predicted wellness or care event, to modify a configuration of at least one of the plurality of sensors, including at least one of a sampling rate or a sensing granularity;

after the configuration of the at least one environmental sensor has been modified, responsive to receiving a token indicating that the wellness or care event has occurred, the at least one processor is configured to:

decode the plurality of tokens with the encryption key, analyze the plurality of tokens, and change the state of the plurality of environmental sensors.

2. The system of claim 1, wherein the at least one processor is further configured to identify potential future states of the person under care by analyzing the digital twin.

3. The system of claim 2, wherein the at least one processor is further configured to identify potential future states of the person under care by analyzing the digital twin and the plurality of tokens.

4. The system of claim 3, wherein the processor uses machine learning to analyze the digital twin and the plurality of tokens.

5. The system of claim 1, wherein the plurality of tokens received from the plurality of environment sensors are encrypted according to an encryption key unique to the person under care.

6. The system of claim 1, wherein modifying the configuration of the plurality of environmental sensors alters a monitoring focus of at least one environmental sensor of the plurality of environmental sensors.

7. The system of claim 6, wherein altering the monitoring focus increases a fidelity or granularity of at least one environmental sensor of the plurality of environmental sensors that was active prior to altering the monitoring focus.

8. The system of claim 1, wherein the plurality of sensors include a breathing sensor, or a heart rate sensor, and the detected data set is from the breathing sensor, or the heart-rate sensor.

9. The system of claim 1, wherein the transceiver is configured to transmit the plurality of tokens to a second care system, wherein the second care system is determined based at least in part on a detected data set from the plurality of environmental sensors.

10. The system of claim 9, wherein the second care system is determined based in part on an at least one stakeholder's relationship to the person under care.

11. The system of claim 10, wherein the at least one stakeholder is determined by data pertinent to the at least one stakeholder's relationship with the person under care.

12. A method to monitor a person under care in an environment by a stakeholder, comprising:

receiving, via a transceiver, a plurality of tokens from a plurality of environmental sensors configured to monitor the person under care, each of the tokens comprising at least in part a detected data set representing behaviors of the person under care, each of the behaviors is represented by a multi-dimensional feature set forming part of a health care profile for the person under care, wherein the token is encrypted using an encryption key;

storing a digital twin of the person under care on a non-transitory computer-readable storage medium, the digital twin comprising a dynamic tokenized representation of quiescent behaviors of the person under care in the environment;

analyzing, via at least one processor, the digital twin of the person under care using a predictive technique to generate a simulated future state of the person under care and the environment, and, based on the simulated future state, determining whether a current configuration of the plurality of environmental sensors is sufficient to detect an actual occurrence of a predicted wellness or care event;

in response to determining that the current configuration of the plurality of environmental sensors is not sufficient to detect the occurrence of the predicted wellness or care event, modifying a configuration of at least one environmental sensor, including at least one of a sampling rate or a sensing granularity; and after modifying the configuration of the at least one environmental sensor, when the wellness or care event has occurred, decoding the plurality of tokens with the encryption key, analyzing the plurality of tokens, and changing the state of the plurality of environmental sensors.

13. The method of claim 12, wherein the plurality of tokens received from the plurality of environmental sensors are encrypted according to an encryption key unique to the person under care.

14. The method of claim 12, wherein modifying the configuration of the plurality of environmental sensors alters a monitoring focus of at least one environmental sensor of the plurality of environmental sensors.

15. A non-transitory computer-readable storage medium encoded with data and instructions when executed by a processor causes a computing device to:

receive, via a transceiver, a plurality of tokens from a plurality of environmental sensors configured to monitor a person under care in an environment, each of the tokens comprising at least in part a detected data set representing behaviors of the person under care in the environment, each of the behaviors is being represented by a multi-dimensional feature set forming part of a health care profile for the person under care, wherein the token is encrypted using an encryption key;

store a digital twin of the person under care on the non-transitory computer-readable storage medium, the digital twin comprising a dynamic tokenized representation of quiescent behaviors of the person under care in the environment;

analyze, via the processor, the digital twin of the person under care using a predictive technique to generate a simulated future state of the person under care and the environment, and, based on the simulated future state, determine whether a current configuration of the plurality of environmental sensors is sufficient to detect an occurrence of a predicted wellness or care event; and in response to determining that the current configuration of the plurality of environmental sensors is not sufficient to detect the occurrence of the predicted wellness or care event, to modify a configuration of at least one environmental sensor, including at least one of a sampling rate or a sensing granularity;

after modifying the configuration of the at least one environmental sensor, when the wellness or care event has occurred, the processor is configured to:

decode the plurality of tokens with the encryption key, analyze the plurality of tokens, and change the state of the plurality of environmental sensors.

16. The non-transitory computer-readable storage medium of claim 15, wherein the digital twin produces predictive future states of the physical environment via a simulated environment.

17. The method of claim 12, further comprising:

storing the plurality of tokens received from the plurality of environmental sensors;

analyzing a sampled subset of the plurality of tokens to confirm a representativeness of a digital twin in reflecting a current state of the physical environment and the person under care; and responsive to determining the digital twin is not representative, adjusting the digital twin according to the sampled subset of the plurality of tokens.

18. The method of claim 12, further comprising:

storing the plurality of tokens for a predetermined time period; and in response to the digital twin indicating that the wellness or care event has been simulated as occurring before the predetermined time period has elapsed, accessing the plurality of tokens that are currently stored.

19. The method of claim 12, further comprising:

in response to the digital twin indicating that the wellness or care event has been simulated as occurring, modifying the configuration of the at least one environmental sensor by changing a rate at which the plurality of tokens are received from the plurality of environmental sensors.

* * * * *